US011977060B1

(12) United States Patent
Fisher et al.

(10) Patent No.: US 11,977,060 B1
(45) Date of Patent: May 7, 2024

(54) METHODS OF DETECTING PREDATORS IN ALGAL CULTURES

(71) Applicants:National Technology & Engineering Solutions of Sandia, LLC, Albuquerque, NM (US); Lawrence Livermore National Laboratory, Livermore, CA (US)

(72) Inventors: Carolyn Laura Fisher, Livermore, CA (US); Todd Lane, Livermore, CA (US); Kristen Leigh Reese, Chester, MA (US); Matthias Frank, Livermore, CA (US)

(73) Assignees: National Technology & Engineering Solutions of Sandia, LLC, Albuquerque, NM (US); Lawrence Livermore National Security, LLC, California (CA)

( * ) Notice: Subject to any disclaimer, the term of this patent is extended or adjusted under 35 U.S.C. 154(b) by 736 days.

(21) Appl. No.: 17/124,596

(22) Filed: Dec. 17, 2020

Related U.S. Application Data

(60) Provisional application No. 62/951,323, filed on Dec. 20, 2019.

(51) Int. Cl.
| | |
|---|---|
| *G01N 30/72* | (2006.01) |
| *C12N 1/12* | (2006.01) |
| *G01N 1/22* | (2006.01) |
| *G01N 1/40* | (2006.01) |
| *G01N 30/02* | (2006.01) |
| *G01N 30/06* | (2006.01) |

(52) U.S. Cl.
CPC ........... *G01N 30/7206* (2013.01); *C12N 1/12* (2013.01); *G01N 1/22* (2013.01); *G01N 1/405* (2013.01); *G01N 2030/025* (2013.01); *G01N 2030/062* (2013.01)

(58) Field of Classification Search
CPC .................................. C12N 1/12; G01N 1/405
See application file for complete search history.

(56) References Cited

U.S. PATENT DOCUMENTS

| | | |
|---|---|---|
| 9,322,014 B1 | 4/2016 | VanderNoot et al. |
| 10,077,454 B1 | 9/2018 | Davis et al. |
| 2005/0014134 A1 | 1/2005 | West et al. |

OTHER PUBLICATIONS

Achyuthan, K.E. et al., "Volatile metabolites emission by in vivo microalgae—an overlooked opportunity?", Metabolites, (Jul. 31, 2017), 7: 39 (46 pp.).
Borowitzka, M.A., "Chapter 14: Culturing microalgae in outdoor ponds", in *Algal Culluring Techniques* (Andersen RA, ed.), (2005), ElseVier Academic Press (Oxford, UK), pp. 205-18.
Carney, L.T. and T.W. Lane, "Parasites in algae mass culture", *Front. Microbiol*, (Jun. 6, 2014), 5: 278 (8 pp.).
Carney, L.T. et al., "Molecular diagnostic solutions in algal cultivation systems", in *Microalgal Production for Biomass and High-Value Products* (Slocombe SP & Benemann JR, eds.), (May 2016), CRC Press (Boca Raton, LA), pp. 183-204 (provided as Sandia Report No. SAND2014-19538B, 27 pp.).
Carney, L.T. et al., "Pond crash forensics: Presumptive identification of pond crash agents by next generation sequencing in replicate raceway mass cultures of *Nannochloropsis salina*", *Algal Res*, (Jul. 2016), 17: 341-7 (provided as Sandia Report No. SAND2015-5591J, 31 pp.).
Christaki, E. et al., "Functional properties of carotenoids originating from algae", *J. Sci. Food Agric*., (Jan. 15, 2013), 93: 5-11.
Day, J.G. et al., "Early detection of protozoan grazers in algal biofuel cultures", *Bioresour. Technol*., (Jun. 2012), 114: 715-9.
Day, J.G. et al., "Microzooplanktonic grazers—a potentially devastating threat to the commercial success of microalgal mass culture", *Algal. Res*., (Nov. 2017), 27: 356-65.
De Jesus Benevides, C.M. et al., "A chemical study of β-carotene oxidation by ozone in an organic model system and the identification of the resulting products", *Food Chem*., (Jun. 1, 2011), 126: 927-34.
Fawley, M.W. et al., "The phylogeny of the genus *Nannochloropsis* (Monodopsidaceae, Eustigmatophyceae), with descriptions of *N. australis* sp. nov. and *Microchloropsis* gen. nov.", *Phycologia* (Apr. 2, 2019), 54: 545-52.
Fisher, C. and T.W. Lane, "Chapter 2: Operational, prophylactic, and interdictive technologies in algal crop protection", in *Grand Challenges in Algae Biotechnology* (Hallmann A & Rampelotto PH, eds.), (Jan. 2019), Springer International Publishing (Cham, Switzerland), pp. 35-70.
Fisher, C.L. et al., "Bacterial communities protect the alga *Microchloropsis salina* from grazing by the rotifer *Brachionus plicatilis*", *Algal Res*., (Apr. 18, 2019), 40: 101500 (9 pp.) (provided as SAND2019-4196J, 11 pp.).
Fisher, C.L. et al., "Low molecular weight volatile organic compounds indicate grazing by the marine rotifer *Brachionus plicatilis* on the microalgae *Microchloropsis salina*", Metabolites, (Sep. 2020), 10(9): 361 (20 pp.).
Fott, B., "*Phlyctidium scenedesmi* spec. nova, a new chytrid destroying mass cultures of algae", *Zeitschrift für allgemeine Mikrobiologie* [*J. Basic Microbiol.*], (1967), 7: 97-102.
Hannon, M. et al., "Biofuels from algae: challenges and potential", *Biofuels*, (Sep. 2010), 1: 763-84.
Havaux, M., "Carotenoid oxidation products as stress signals in plants", *Plant J*., (Nov. 25, 2013), 79: 597-606.
Hay, M.E., "Marine chemical ecology: chemical signals and cues structure marine populations, communities, and ecosystems", *Ann. Rev. Mar. Sci*., (Jan. 2009), 1: 193-212.
Hirayama, K. and S. Ogawa, "Fundamental studies on physiology of rotifer for its mass culture-I: filter feeding of rotifer", *Nippon Suisan Gakkaishi* [*Bull. Japan. Soc. Sci. Fisheries*], (1972), 38: 1207-14.

(Continued)

*Primary Examiner* — Ruth A Davis
(74) *Attorney, Agent, or Firm* — Eschweiler & Potashnik, LLC; Madelynne J. Farber; Samantha Updegraff

(57) ABSTRACT

The present disclosure features methods of detecting crop damage in an algal culture. Such methods include detecting one or more carotenoids as a volatile organic compound in a sample obtained from a headspace of the algal culture.

20 Claims, 26 Drawing Sheets

(56) References Cited

OTHER PUBLICATIONS

Isleten Hosoglu, M., "Aroma characterization of five microalgae species using solid-phase microextraction and gas chromatography-mass spectrometry/olfactometry", *Food Chem.*, (Feb. 1, 2018), 240: 1210-8.

Jüttner, F. et al., "β-cyclocitral, a grazer defence signal unique to the cyanobacterium Microcystis", *J. Chem. Ecol.*, (Nov. 12, 2010), 36: 1387-97.

Katiyar, R. et al., "Microalgae based biofuel: challenges and opportunities", in *Biofuels: Technology, Challenges and Prospects* (Agarwal AK, Agarwal RA, Gupta T, & Gurjar BR, eds.), (Feb. 2017), Springer Singapore (Singapore), pp. 157-175.

Leach, J.E. et al., "Communication in the phytobiome", *Cell*, (May 4, 2017), 169: 587-96.

Leite, G.B. et al., "Algal biofuels: challenges and opportunities", *Bioresour. Technol.*, (Oct. 1, 2013), 145: 134-41 (30 pp.).

Lewis, P.R. et al., "Recent advancements in the gas-phase MicroChemLab", *IEEE Sensors J.*, (Jun. 5, 2006), 6: 784-95.

Liu, Z. et al., "Studies on Killing *Euplotes* Sp. & *Oxyrrhis* Sp. in the Culture Liquid of Marine Unicellular Alge," *Zhanjiang Fisheries College* (Dec. 1990) 10(2):36-41 (English Abstract).

Mcbride, R.C. et al., "Contamination management in low cost open algae ponds for biofuels production", *Indust. Biotechnol.*, (Jun. 5, 2014), 10: 221-7.

Park, S. et al., "The selective use of hypochlorite to prevent pond crashes for algae-biofuel production", *Water Environ. Res.*, (Jan. 2016), 88: 70-8.

Pradeep, V. et al., "Use of copper to selectively inhibit *Brachionus calyciflorus* (predator) growth in *Chlorella kessleri* (prey) mass cultures for algae biodiesel production", *Int. J. Mol. Sci.*, (Aug. 31, 2015), 16: 20674-84.

Ramel, F. et al., "Carotenoid oxidation products are stress signals that mediate gene responses to singlet oxygen in plants", *Proc. Nat'l Acad. Sci. USA* (Apr. 3, 2012), 109: 5535-40.

Reese, K.L. et al., "Chemical profiling of volatile organic compounds in the headspace of algal cultures as early biomarkers of algal pond crashes", *Sci. Rep.*, (Sep. 25, 2019), 9: 13866 (10 pp.) and Supplemental Data File (15 pp.).

Richardson, J.W. et al., "A financial assessment of two alternative cultivation systems and their contributions to algae biofuel economic viability", *Algal Res.*, (Jan. 8, 2014), 4: 96-104.

Rowan, D.D., "Volatile metabolites", *Metabolites*, (Nov. 25, 2011), 1: 41-63.

Snyder, D.T. et al., "Miniature and fieldable mass spectrometers: recent advances", *Anal. Chem* (Jan. 5, 2016), 88: 2-29.

United States Department of Energy, "Bioenergy Technologies Office: Multi-Year Program Plan", *DOE Report No. DOE/EE-0915*, Washington, DC, (May 2013) (190 pp.).

Van Durme, J. et al., "Evaluation of the volatile composition and sensory properties of five species of microalgae", *J. Agric. Food Chem.*, (Nov. 5, 2013), 61: 10881-90.

Van Ginkel, S.W. et al., "Taking advantage of rotifer sensitivity to rotenone to prevent pond crashes for algal-biofuel production", *Algal Res.*, (Jul. 2015), 10: 100-3.

Wang, H. et al., "The contamination and control of biological pollutants in mass cultivation of microalgae", *Bioresour. Technol.*, (Jan. 2013), 128: 745-50.

Wang, Y. et al., "Early detection and quantification of zooplankton grazers in algal cultures by FlowCAM", *Algal Res.* (Jan. 2017), 21: 98-102.

Whiting, J.J. et al., "A high-speed, high-performance, microfabricated comprehensive two-dimensional gas chromatograph", *Lab Chip*, (Apr. 23, 2019), 19: 1633-43 (provided as SAND2019-3452J, 15 pp.).

Winterhalter, P. and R. Rouseff, "Chapter 1, Carotenoid-derived aroma compounds: an introduction", in *Carotenoid-Derived Aroma Compounds* (Winterhalter P & Rouseff RL, eds.), (Nov. 2001), American Chemical Society (Washington, DC), pp. 1-17.

Wolfe, G.V. and M. Steinke, "Grazing-activated production of dimethyl sulfide (DMS) by two clones of *Emiliania huxleyi*", *Limnol. Oceanogr.*, (Sep. 1996), 41: 1151-60.

Wolfe, G.V. et al., "Grazing-activated chemical defence in a unicellular marine alga", *Nature*, (Jun. 26, 1997), 387: 894-7.

Wolfe, G.V. et al., "Release and consumption of DMSP from *Emiliania huxleyi* during grazing by *Oxyrrhis marina*", *Mar. Ecol. Prog. Ser.*, (Aug. 11, 1994), 111: 111-9.

Xu, C. et al., "The use of the schizonticidal agent quinine sulfate to prevent pond crashes for algal-biofuel production", *Int. J. Mol. Sci.* (Nov. 17, 2015), 16: 27450-6.

Zhou, L. et al., "Change of volatile components in six microalgae with different growth phases", *J. Sci. Food Agric.*, (Jun. 7, 2016), 97: 761-9.

Zuo, Z., "Why algae release volatile organic compounds—the emission and roles", *Front. Microbiol.* (Mar. 12, 2019), 10: 491 (7 pp.).

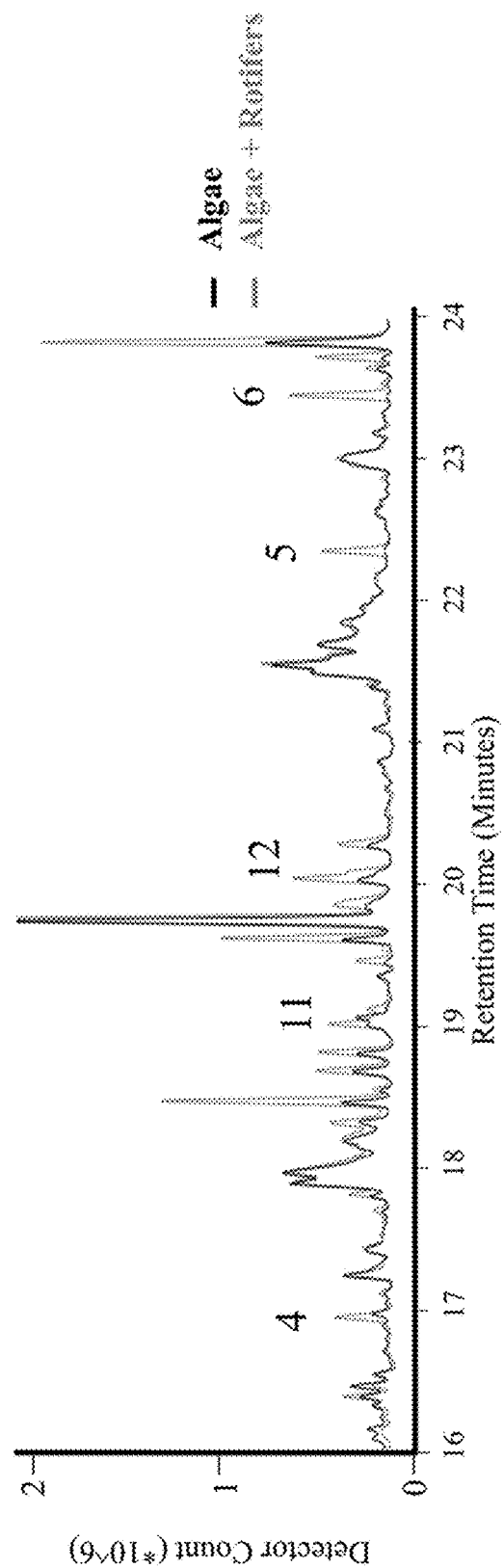
FIG. 7A
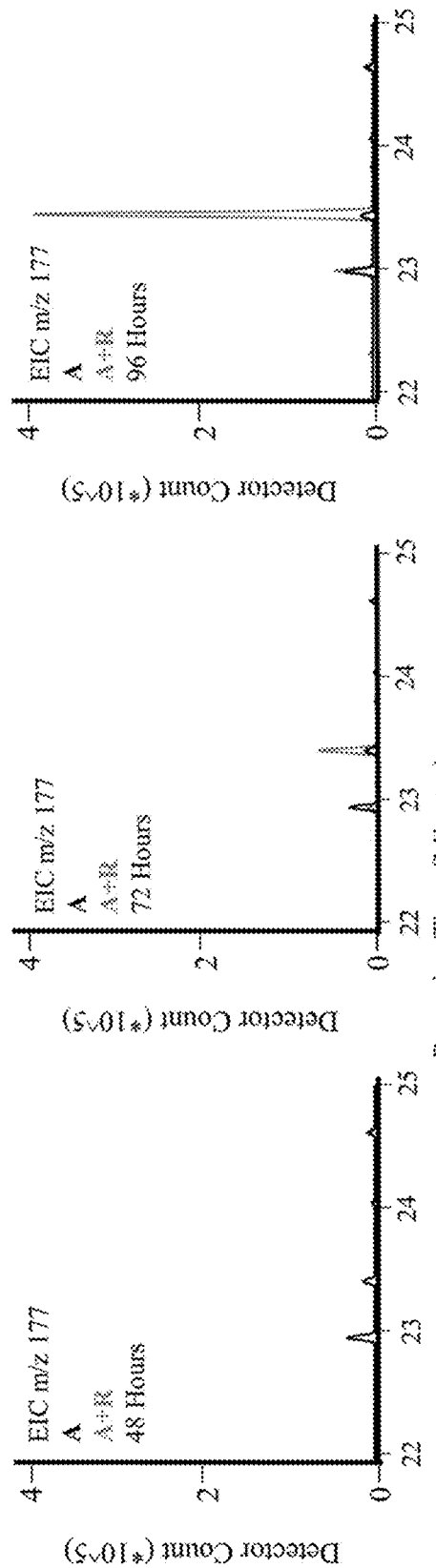
FIG. 7B
FIG. 7C
FIG. 7D

US 11,977,060 B1

METHODS OF DETECTING PREDATORS IN ALGAL CULTURES

CROSS-REFERENCE TO RELATED APPLICATION

This application claims the benefit of U.S. Provisional Application No. 62/951,323, filed Dec. 20, 2019, which is incorporated herein by reference in its entirety.

STATEMENT OF GOVERNMENT INTEREST

This invention was made with Government support under Contract No. DE-AC52-07NA27344 awarded by the United States Department of Energy and under Contract No. DE-NA0003525 awarded by the United States Department of Energy/National Nuclear Security Administration. The Government has certain rights in the invention.

FIELD

The present disclosure features methods of detecting crop damage in an algal culture. Such methods include detecting one or more carotenoids as a volatile organic compound in a sample obtained from a headspace of the algal culture.

BACKGROUND

Algal cultures can be a viable, renewable resource for sustainable energy and chemical production. Cost-effective production remains a challenge. For instance, entire crops of algae can be lost or infected due to various factors, e.g., parasitism, resulting in contaminated cultures that are difficult to remediate. Additional mitigation strategies are required.

SUMMARY

The present disclosure relates, in part, to non-invasive methods of detecting crop damage in an algal culture. We have identified volatile organic compounds (VOCs) that serve as a chemical biomarker for pathogens within the culture. In particular, the VOCs are present within a gaseous sample obtained in proximity to the culture (e.g., a sample obtained from the headspace of the culture). As described herein, in some embodiments, the VOC is an oxidized carotenoid (e.g., β-ionone, β-cyclocitral, as well as any described herein).

In a first aspect, the present disclosure features a method of detecting crop damage (e.g., from a parasite, a grazer, a pathogen, a rotifer, or any described herein) in an algal culture, the method including: detecting one or more carotenoids as a VOC within a first sample (e.g., a first gaseous sample) obtained from a headspace of the algal culture, thereby indicating presence of crop damage (e.g., any described herein).

In some embodiments, the carotenoid has a structure of formula (I), (II), or a salt thereof (e.g., any described herein). In other embodiments, the carotenoid is an oxidized form of a compound having a structure of formula (IIIa), (IIIb), (IV), (V), or a salt thereof (e.g., any described herein).

In some embodiments, the carotenoid is trans-β-ionone, β-cyclocitral, 2,2,6-trimethylcyclohexanone, and/or 4-(2,6, 6-trimethyl-1-cyclohexen-1-yl)-2-butanone. In some embodiments, the method includes detecting two or more carotenoids.

In some embodiments, the method further includes detecting one or more further carotenoids as a VOC within a second sample obtained from the headspace of the algal culture.

In particular embodiments, the second sample is obtained of from about 5 minutes to about 72 hours after the first sample (e.g., from about 5 minutes to 30 minutes, 5 minutes to 1 hour, 5 minutes to 2 hours, 5 minutes to 6 hours, 5 minutes to 12 hours, 5 minutes to 24 hours, 5 minutes to 36 hours, 5 minutes to 48 hours, 5 minutes to 60 hours, 10 minutes to 30 minutes, 10 minutes to 1 hour, 10 minutes to 2 hours, 10 minutes to 6 hours, 10 minutes to 12 hours, 10 minutes to 24 hours, 10 minutes to 36 hours, 10 minutes to 48 hours, 10 minutes to 60 hours, 10 minutes to 72 hours, 30 minutes to 1 hour, 30 minutes to 2 hours, 30 minutes to 6 hours, 30 minutes to 12 hours, 30 minutes to 24 hours, 30 minutes to 36 hours, 30 minutes to 48 hours, 30 minutes to 60 hours, 30 minutes to 72 hours, 1 hour to 2 hours, 1 hour to 6 hours, 1 hour to 12 hours, 1 hour to 24 hours, 1 hour to 36 hours, 1 hour to 48 hours, 1 hour to 60 hours, or 1 hour to 72 hours).

In some embodiments, the carotenoid from the first sample and the further carotenoid from the second sample are the same. In other embodiments, a detected amount of the further carotenoid from the second sample is greater than a detected amount of the carotenoid from the first sample.

In another aspect, the present disclosure features a method of detecting crop damage (e.g., from a parasite, a grazer, a pathogen, a rotifer, or other described herein) in an algal culture, the method including: detecting one or more carotenoids as a VOC within a first sample (e.g., a first gaseous sample) obtained from a headspace of the algal culture; and further detecting the one or more carotenoids as a VOC within a second sample (e.g., a second gaseous sample) obtained from the headspace of the algal culture, wherein the second sample is obtained after the first sample. In some embodiments, the method thereby indicates the presence of crop damage.

In some embodiments, the carotenoid (e.g., in the first and/or second sample) has a structure of formula (I), (II), or a salt thereof (e.g., any described herein). In other embodiments, the carotenoid (e.g., in the first and/or second sample) is an oxidized form of a compound having a structure of formula (IIIa), (IIIb), (IV), (V), or a salt thereof (e.g., any described herein).

In some embodiments, the carotenoid (e.g., in the first and/or second sample) is trans-β-ionone, β-cyclocitral, 2,2, 6-trimethylcyclohexanone, and/or 4-(2,6,6-trimethyl-1-cyclohexen-1-yl)-2-butanone. In other embodiments, the method includes detecting two or more carotenoids in each sample (e.g., in the first and/or second sample).

In some embodiments, the second sample is obtained of from about 10 minutes to about 72 hours after the first sample (e.g., from about 5 minutes to 30 minutes, 5 minutes to 1 hour, 5 minutes to 2 hours, 5 minutes to 6 hours, 5 minutes to 12 hours, 5 minutes to 24 hours, 5 minutes to 36 hours, 5 minutes to 48 hours, 5 minutes to 60 hours, 10 minutes to 30 minutes, 10 minutes to 1 hour, 10 minutes to 2 hours, 10 minutes to 6 hours, 10 minutes to 12 hours, 10 minutes to 24 hours, 10 minutes to 36 hours, 10 minutes to 48 hours, 10 minutes to 60 hours, 10 minutes to 72 hours, 30 minutes to 1 hour, 30 minutes to 2 hours, 30 minutes to 6 hours, 30 minutes to 12 hours, 30 minutes to 24 hours, 30 minutes to 36 hours, 30 minutes to 48 hours, 30 minutes to 60 hours, 30 minutes to 72 hours, 1 hour to 2 hours, 1 hour to 6 hours, 1 hour to 12 hours, 1 hour to 24 hours, 1 hour to 36 hours, 1 hour to 48 hours, 1 hour to 60 hours, or 1 hour to 72 hours).

In some embodiments, a detected amount of the carotenoid from the second sample is greater than a detected amount of the carotenoid from the first sample. In particular embodiments, a detected amount of trans-β-ionone and/or β-cyclocitral from the second sample is greater than a detected amount of the trans-β-ionone and/or β-cyclocitral from the first sample.

In any embodiment herein, the detecting step and/or the further detecting step includes employing one or more solid-phase microextraction fibers (e.g., configured to capture the volatile organic compound) coupled with gas chromatography-mass spectrometry (e.g., configured to detect the one or more carotenoids).

In any embodiment herein, method further includes (e.g., after the further detecting step): providing one or more additives to protect the algal culture. Additional details follow.

Definitions

As used herein, the term "about" means +/−10% of any recited value. As used herein, this term modifies any recited value, range of values, or endpoints of one or more ranges.

The term "acyl," or "alkanoyl," as used interchangeably herein, represent an alkyl group, as defined herein, an alkenyl group, as defined herein, or hydrogen attached to the parent molecular group through a carbonyl group, as defined herein. This group is exemplified by formyl, acetyl, propionyl, butanoyl, and the like. The alkanoyl group can be substituted or unsubstituted. For example, the alkanoyl group can be substituted with one or more substitution groups, as described herein for alkyl. In some embodiments, the unsubstituted acyl group is a $C_{1-24}$ acyl or alkanoyl group. In some embodiments, the unsubstituted acyl group is a $C_{1-3}$, $C_{1-6}$, $C_{1-12}$, $C_{1-16}$, $C_{1-18}$, $C_{1-20}$, or $C_{1-24}$ acyl group.

By "alkenal" is meant a compound having an optionally substituted $C_{2-24}$ alkenyl group (e.g., as defined herein) attached to a carboxyaldehyde (e.g., a —C(O)H group). In some embodiments, the unsubstituted alkenal is a $C_{2-6}$, $C_{2-10}$, $C_{2-12}$, $C_{2-20}$, $C_{2-24}$, $C_{6-10}$, $C_{6-12}$, $C_{6-20}$, $C_{6-24}$, $C_{7-10}$, $C_{7-12}$, $C_{7-20}$, or $C_{7-24}$ alkenal.

By "alkenyl" is meant an optionally substituted $C_{2-24}$ alkyl group having one or more double bonds. The alkenyl group can be cyclic (e.g., $C_{3-24}$ cycloalkenyl) or acyclic. The alkenyl group can also be substituted or unsubstituted. For example, the alkenyl group can be substituted with one or more substitution groups, as described herein for alkyl. In some embodiments, the unsubstituted alkenyl group is a $C_{2-3}$, $C_{2-6}$, $C_{2-12}$, $C_{2-16}$, $C_{2-18}$, $C_{2-20}$, or $C_{2-24}$ alkenyl group. In other embodiments, the unsubstituted alkenyl group is a Cn alkenyl group having n/2 number of double bonds, where n is a number (e.g., an even number) of from about 2 to 24.

By "alkenylene" is meant a multivalent (e.g., bivalent, trivalent, tetravalent, etc.) form of an alkenyl group, as described herein. In some embodiments, the alkenylene group is a $C_{2-3}$, $C_{2-6}$, $C_{2-12}$, $C_{2-16}$, $C_{2-18}$, $C_{2-20}$, or $C_{2-24}$ alkylene group. The alkenylene group can be branched or unbranched. The alkenylene group can also be substituted or unsubstituted. For example, the alkenylene group can be substituted with one or more substitution groups, as described herein for alkyl. In other embodiments, the unsubstituted alkenylene group is a Cn alkenylene group having n/2 number of double bonds, where n is a number (e.g., an even number) of from about 2 to 24.

By "alkyl" and the prefix "alk" is meant a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic (e.g., $C_{3-24}$ cycloalkyl) or acyclic. The alkyl group can be branched or unbranched. The alkyl group can also be substituted or unsubstituted. For example, the alkyl group can be substituted with one, two, three or, in the case of alkyl groups of two carbons or more, four substituents independently selected from the group consisting of: (1) $C_{1-6}$ alkoxy (e.g., —OAk, in which Ak is an alkyl group, as defined herein); (2) $C_{1-6}$ alkylsulfinyl (e.g., —S(O)Ak, in which Ak is an alkyl group, as defined herein); (3) $C_{1-6}$ alkylsulfonyl (e.g., —SO$_2$Ak, in which Ak is an alkyl group, as defined herein); (4) amino (e.g., —NR$^{N1}$R$^{N2}$, where each of R$^{N1}$ and R$^{N2}$ is, independently, H or optionally substituted alkyl, or R$^{N1}$ and R$^{N2}$, taken together with the nitrogen atom to which each are attached, form a heterocyclyl group); (5) aryl; (6) arylalkoxy (e.g., —OA$^L$Ar, in which A$^L$ is an alkylene group and Ar is an aryl group, as defined herein); (7) aryloyl (e.g., —C(O)Ar, in which Ar is an aryl group, as defined herein); (8) azido (e.g., an —N$_3$ group); (9) cyano (e.g., a —CN group); (10) carboxyaldehyde (e.g., a —C(O)H group); (11) $C_{3-8}$ cycloalkyl; (12) halo; (13) heterocyclyl (e.g., a 5-, 6- or 7-membered ring, unless otherwise specified, containing one, two, three, or four non-carbon heteroatoms (e.g., independently selected from the group consisting of nitrogen, oxygen, phosphorous, sulfur, or halo)); (14) heterocyclyloxy (e.g., —OHet, in which Het is a heterocyclyl group); (15) heterocyclyloyl (e.g., —C(O) Het, in which Het is a heterocyclyl group); (16) hydroxyl (e.g., a —OH group); (17) N-protected amino; (18) nitro (e.g., an —NO$_2$ group); (19) oxo (e.g., an =O group); (20) $C_{3-8}$ spirocyclyl (e.g., an alkylene diradical, both ends of which are bonded to the same carbon atom of the parent group to form a spirocyclyl group); (21) $C_{1-6}$ thioalkoxy (e.g., —SAk, in which Ak is an alkyl group, as defined herein); (22) thiol (e.g., an —SH group); (23) —CO$_2$R$^A$, where R$^A$ is selected from the group consisting of (a) hydrogen, (b) $C_{1-6}$ alkyl, (c) $C_{4-18}$ aryl, and (d) $C_{1-6}$ alk-$C_{4-18}$ aryl; (24) —C(O)NR$^B$R$^C$, where each of R$^B$ and R$^C$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; (25) —SO$_2$RD, where RD is selected from the group consisting of (a) $C_{1-6}$ alkyl, (b) $C_{4-18}$ aryl, and (c) $C_{1-6}$ alk-$C_{4-18}$ aryl; (26) —SO$_2$NR$^E$R$^F$, where each of R$^E$ and R$^F$ is, independently, selected from the group consisting of (a) hydrogen, (b) $C_{1-6}$ alkyl, (c) $C_{4-18}$ aryl, and (d) $C_{1-6}$ alk-$C_{4-18}$ aryl; and (27) —NR$^G$R$^H$, where each of R$^G$ and R$^H$ is, independently, selected from the group consisting of (a) hydrogen, (b) an N-protecting group, (c) $C_{1-6}$ alkyl, (d) $C_{2-6}$ alkenyl, (e) $C_{2-6}$ alkynyl, (f) $C_{4-18}$ aryl, (g) $C_{1-6}$ alk-$C_{4-18}$ aryl, (h) $C_{3-8}$ cycloalkyl, and (i) $C_{1-6}$ alk-$C_{3-8}$ cycloalkyl, wherein in one embodiment no two groups are bound to the nitrogen atom through a carbonyl group or a sulfonyl group. The alkyl group can be a primary, secondary, or tertiary alkyl group substituted with one or more substituents (e.g., one or more halo or alkoxy). In some embodiments, the unsubstituted alkyl group is a $C_{1-3}$, $C_{1-6}$, $C_{1-12}$, $C_{1-16}$, $C_{1-18}$, $C_{1-20}$, or $C_{1-24}$ alkyl group.

By "alkylene" is meant a multivalent (e.g., bivalent, trivalent, tetravalent, etc.) form of an alkyl group, as described herein. Exemplary alkylene groups include methylene, ethylene, propylene, butylene, etc. In some embodiments, the alkylene group is a $C_{1-3}$, $C_{1-6}$, $C_{1-12}$, $C_{1-16}$, $C_{1-18}$, $C_{1-20}$, $C_{1-24}$, $C_{2-3}$, $C_{2-6}$, $C_{2-12}$, $C_{2-16}$, $C_{2-18}$, $C_{2-20}$, or $C_{2-24}$ alkylene group. The alkylene group can be branched or unbranched. The alkylene group can also be substituted or unsubstituted. For example, the alkylene group can be substituted with one or more substitution groups, as described herein for alkyl.

By "cycloalkyl" is meant a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl group can also be substituted or unsubstituted. For example, the cycloalkyl group can be substituted with one or more groups including those described herein for alkyl.

By "cycloalkenyl" is meant a cycloalkyl group, as defined herein, having one or more double bonds. The cycloalkenyl group can also be substituted or unsubstituted. For example, the cycloalkenyl group can be substituted with one or more groups including those described herein for alkyl.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," *J. Pharm. Sci.* 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the disclosure or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the disclosure will be apparent from the following description and the claims.

BRIEF DESCRIPTION OF THE DRAWINGS

FIGS. 7A-7D show example chromatograms for observed VOCs sampled from Algae (indicated as "A") and Algae+

Rotifer (indicated as "A+R") cultures between 16 and 24 min. Provided are (A) total ion chromatogram with indicated VOCs (see annotations in Table 3) and (B-D) extracted ion chromatograms monitoring increase in Compound 6 over time (m/z of 177, retention index (RI) of 1495).

Figure 8:
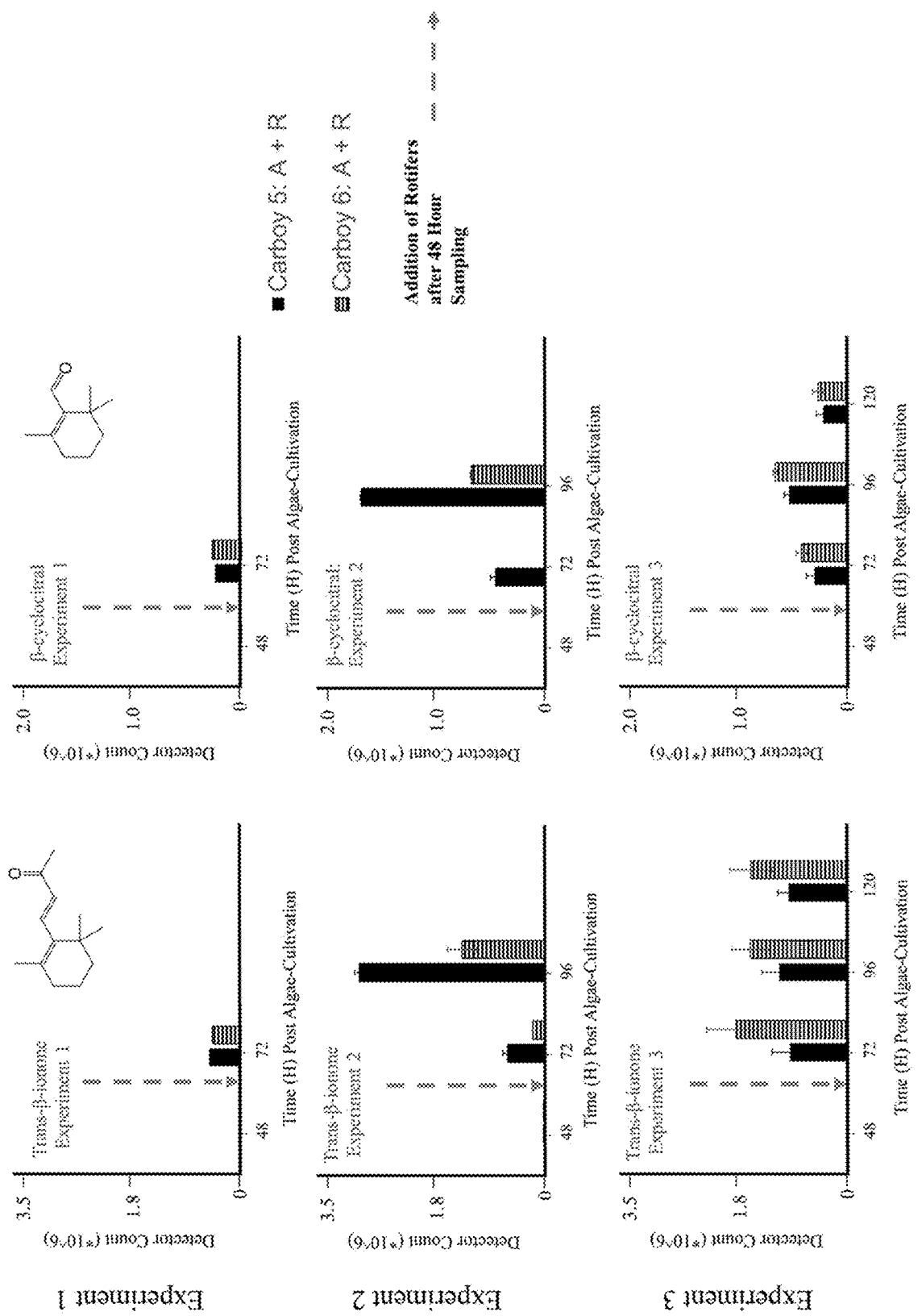

FIG. 8 shows peak areas of extracted compound chromatograms for trans-β-ionone and β-cyclocitral across Experiments 1, 2, and 3, separated by biological replicates. Error bars represent standard deviation derived from duplicate measurements for each sample. The exposure time for SPME fibers was 30 minutes in Experiment 1 and 60 minutes in Experiments 2 and 3.

Figure 9A:
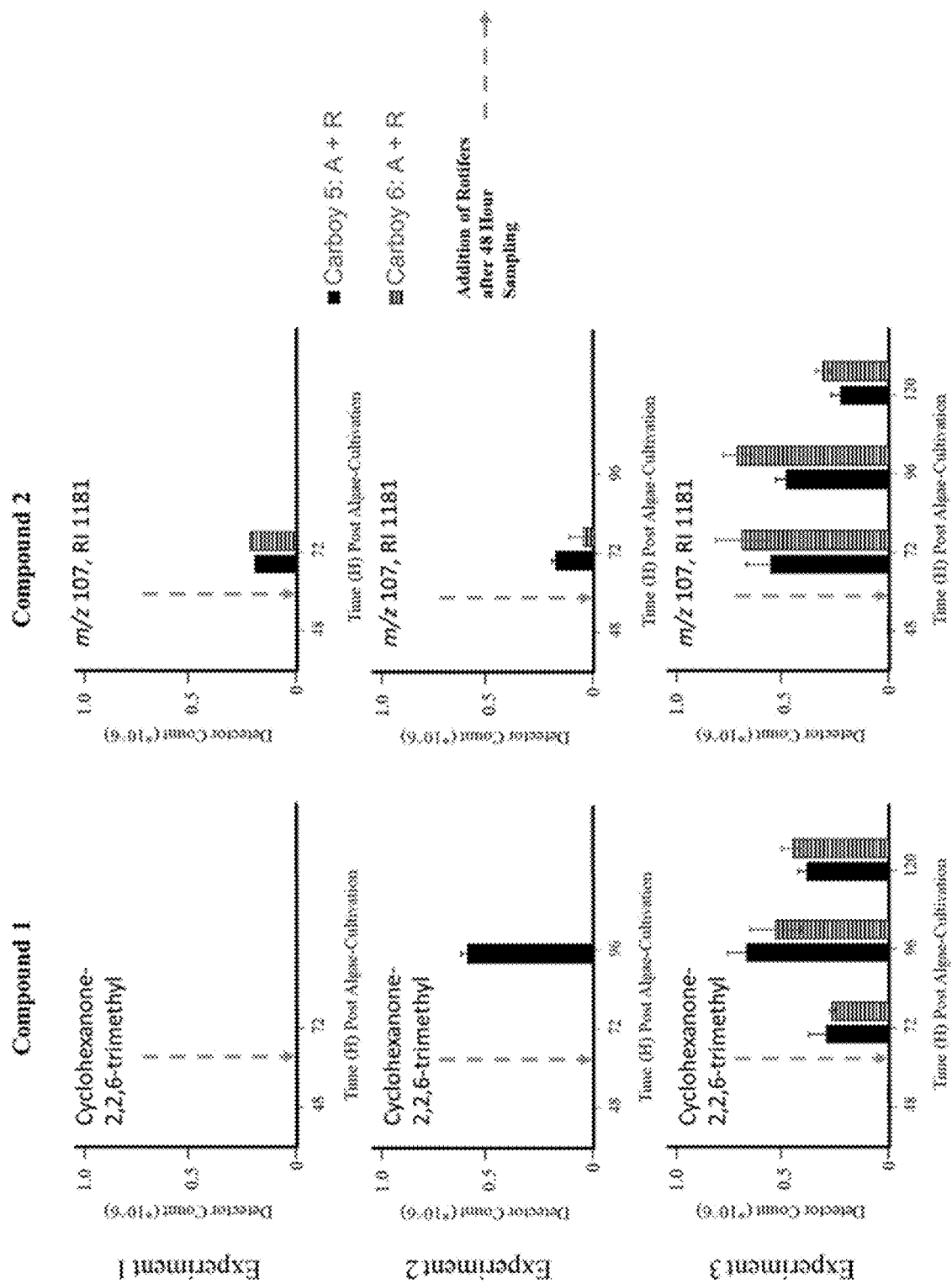
Figure 9B:
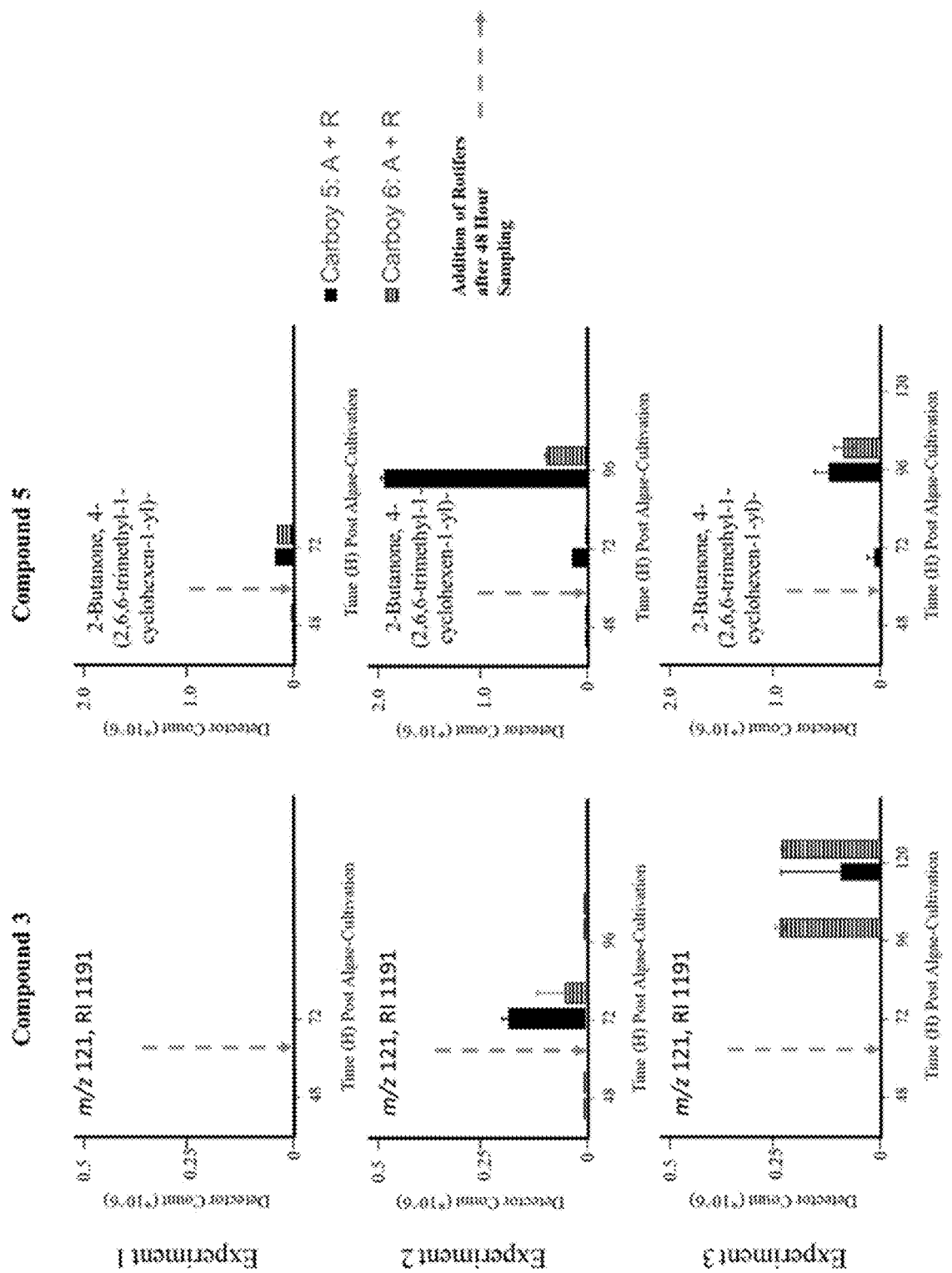
Figure 9C:
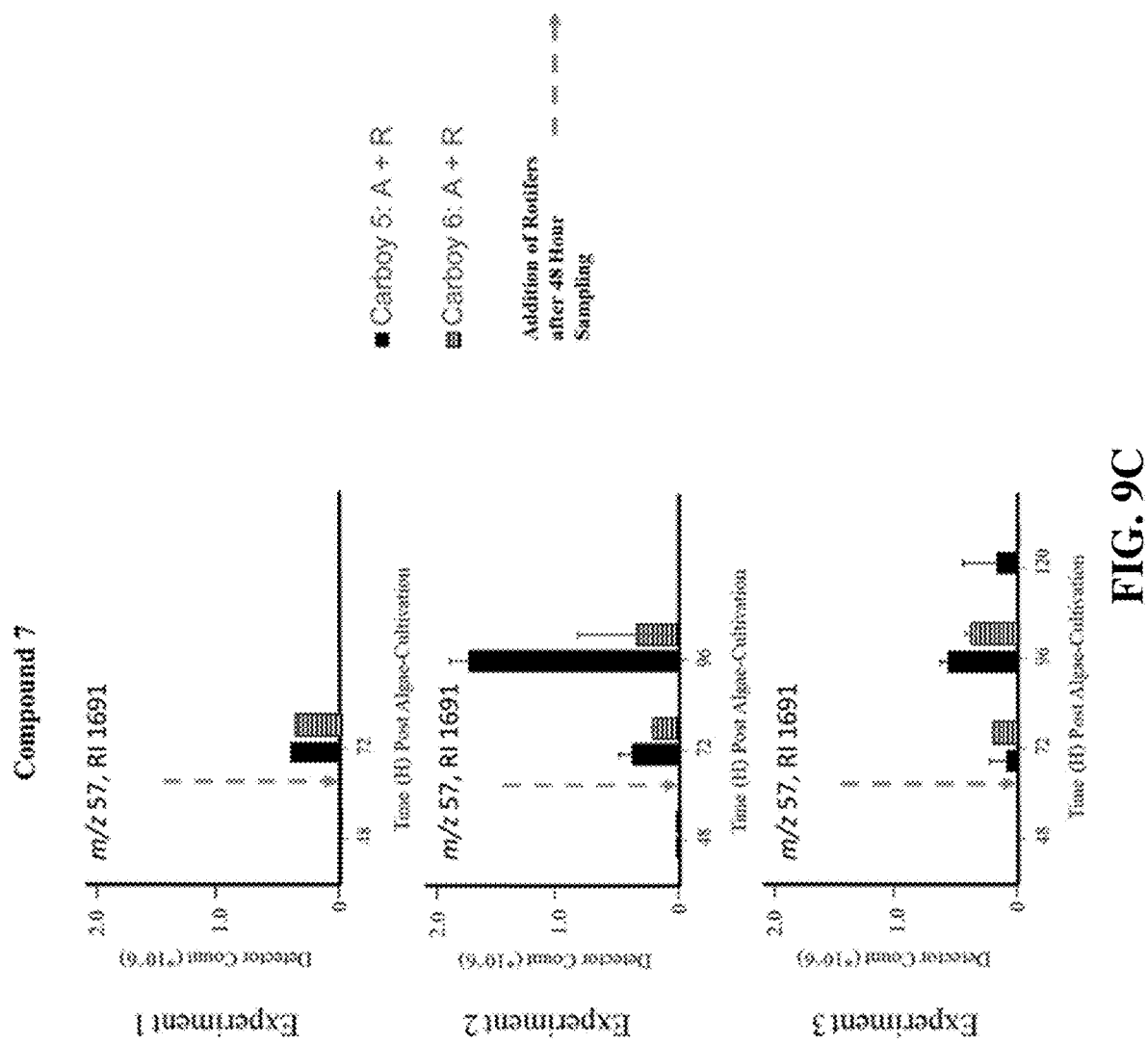

FIGS. 9A-9C show peak areas of extracted compound chromatograms for (A) Compounds 1 and 2, (B) Compounds 3 and 5, and (C) Compound 7 across Experiments 1, 2, and 3. Data from Compounds 4 and 6 are displayed in FIG. 8.

Figure 10:
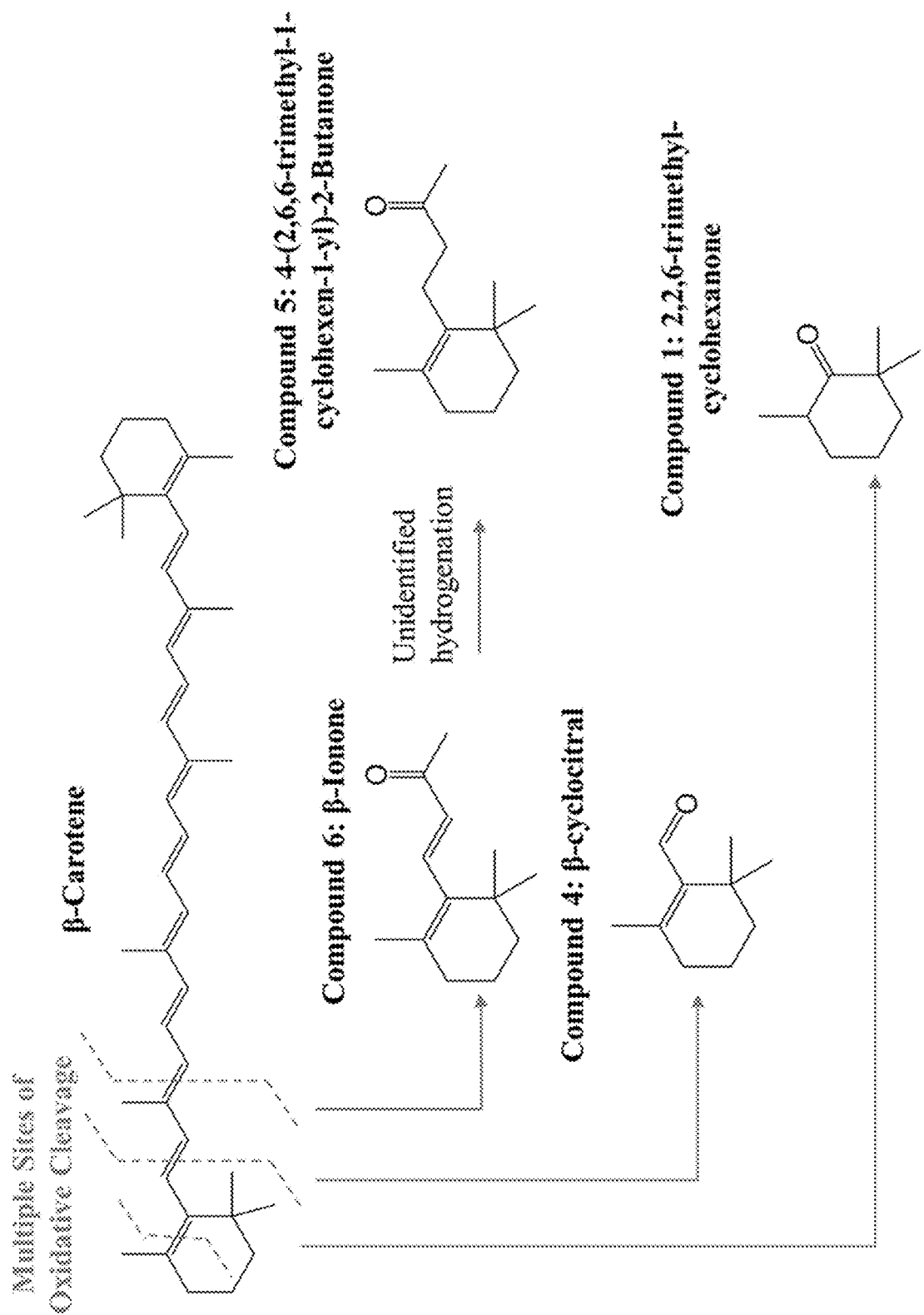

FIG. 10 shows exemplary VOCs identified from the headspace of A+R cultures formed from the oxidative cleavage of the carotenoid β-carotene. Exemplary oxidation cleavages relevant to this study are pictured, but all double bonds across the β-carotene backbone are cleaved.

DETAILED DESCRIPTION

The present disclosure relates, in part, to detecting one or more compounds (e.g., carotenoids) within a sample obtained from a headspace of a culture. In some embodiments, the headspace refers to an area above algal culture, thereby ensuring that the area includes a gas phase residing above the culture. A sample can be captured or obtained from the headspace of the culture by using any useful methodology, e.g., by use of solid-phase microextraction (SPME), as well as any described herein. In particular embodiments, the sample is a gaseous sample having one or more volatile organic compounds (VOCs).

Figure 1A:
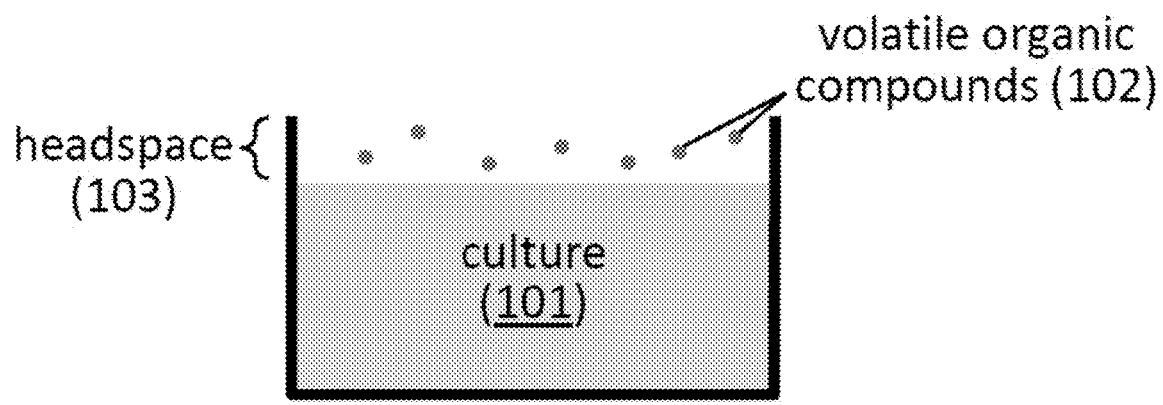
FIGS. 1A-1C show exemplary schematics of cultures and volatile organic compounds (VOCs). Provided herein are (A) a schematic of an algal culture 101 having VOCs 102 in the headspace 103 of the culture; (B) a schematic of an infected algal culture 201 having VOCs 202 in the headspace 203 of the culture; and (C) a schematic of a compound having a structure of formula (V), in which oxidation of that compound provides a carotenoid having a structure of formula (I).
Figure 1B:
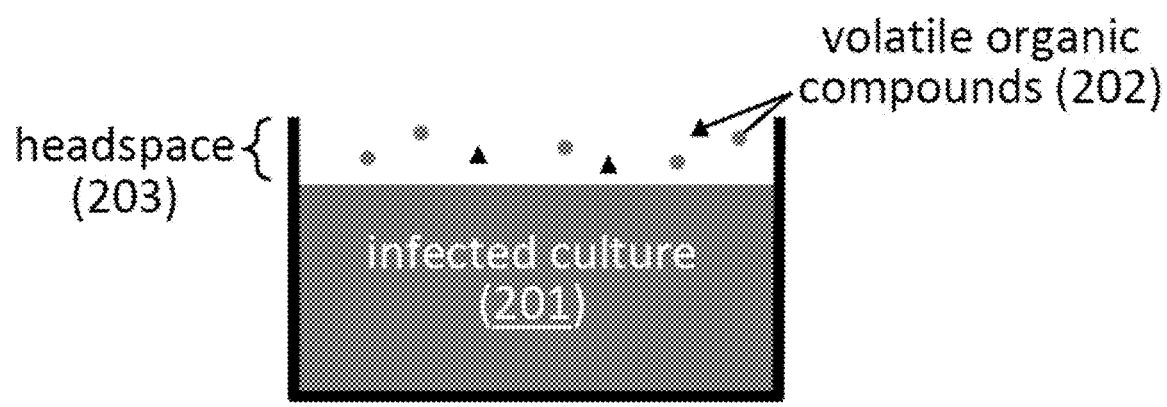

FIG. 1A shows an exemplary algal culture 101 characterized by a headspace 103 disposed above the culture. Within that headspace, VOCs 102 may be present, whether due to metabolic growth or development of that culture. Such VOCs can act as chemical biomarkers of intraspecies or interspecies communication and interaction. Thus, we suspected that stressed or infected cultures could emit VOC signatures that could be used to distinguished from VOCs present in a healthy, thriving culture. FIG. 1B shows an exemplary infected algal culture 201 (e.g., infected with a grazer) having VOCs 202 disposed within the headspace 203. Here, the VOCs include the presence of one or more biomarkers indicative of the presence of the pathogen (e.g., biomarkers, such as a carotenoid, including any described herein) or other type of crop damage, as described herein.

Figure 1C:
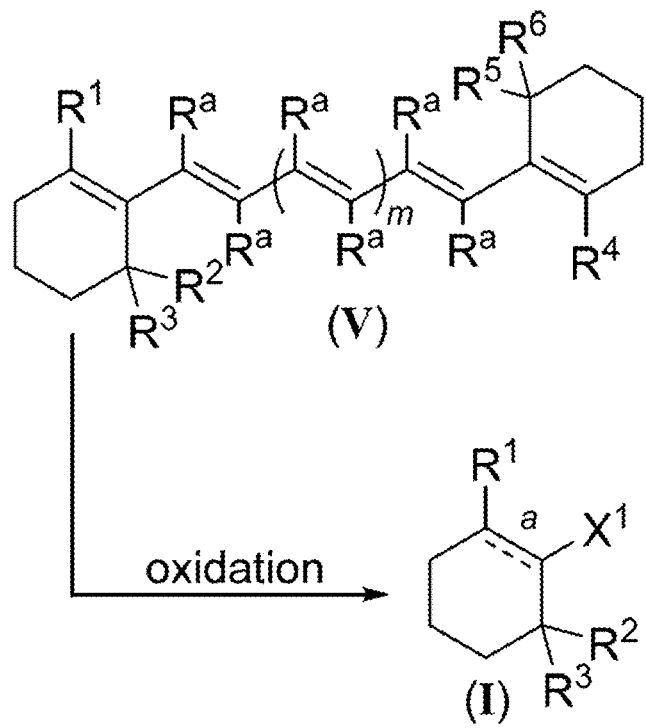

In some instances, the biomarker is a VOC derived from carotene or carotenoids, including oxidized forms thereof. As seen in FIG. 1C, an exemplary carotene-derived compound includes a compound having a structure of formula (V), in which exemplary moieties for $R^1$, $R^2$, $R^3$, $R^4$, $R^5$, $R^6$, and $R^a$ are described herein. Oxidation of such a compound can include any useful carotenoid, such as a compound having a structure of formula (I), in which exemplary moieties for $R^1$, $R^2$, $R^3$, and $X^1$ are described herein. The presence of such a carotenoid can arise from the presence of crop damage. In one non-limiting instance, release of such carotenoids results from a grazer grazing and digestion of algal cells, in which the chemical characteristics of the released carotenoid result in emission of that carotenoid as a VOC in the headspace. In another instance, release of such carotenoids results from a parasite, a grazer (e.g., zooplankton), a pathogen (e.g., a virus, bacterium, or fungus), a contaminant, or other chemical compound being in the presence of algal cells.

Such VOCs can have any useful characteristic. In some embodiments, the VOC is a carbon-containing molecule with a high vapor pressure (e.g., a vapor pressure greater than about 10 Pa, such as of from about 10 Pa to 70 kPa) at an ambient temperature (e.g., a temperature of about 20° C. and pressure of 101.3 kPa). In other embodiments, the VOC is a carbon-containing molecule with an initial boiling point less than or equal to about 250° C. (e.g., an initial boiling point of from about 40° C. to about 260° C.). In particular embodiments, the VOC has a molecular weight of from about ~200 g/mol. Exemplary VOCs can include one or more carotenoids, including oxidized carotenoids (e.g., any described herein); alcohols (e.g., aliphatic or cyclic alcohols, such as an alkanol (e.g., hexanol), an alkenol (e.g., hexenol), or a cyclic alcohol (2-methylisoborneol or geosmin)); aldehydes (e.g., alkenals, such as $C_{7-12}$ alkenals, including two double bonds (dienals) or three double bonds (trienals), e.g., 2,4-heptadienal, 2,4-decadienal, or 2,4,7-decatrienal); hydrocarbons (e.g., aliphatic hydrocarbons, including $C_{15-21}$ hydrocarbons; alkenes having one or more double bonds, including $C_{7-10}$ alkenes (e.g., dienes having two double bonds or trienes having three double bonds); cyclic hydrocarbons; as well as aromatic hydrocarbons, including benzene or naphthalene); fatty acids (e.g., short-chain fatty acids, such as $C_{2-6}$ fatty acids, including acetic acid, butyric acid, or propionic acid); etc.

Such VOCs can be captured and analyzed with any useful methodology, and such capture and detection methodologies can be employed together in any useful manner. Exemplary capture methodologies include closed loop stripping analysis (CLSA), simultaneous distillation extraction (SDE), solvent microextraction (SME), solid phase extraction (SPE), solid-phase microextraction (SPME), thermal desorption (TD), liquid impingement, and/or grab sampling. Optionally, one or more VOCs may be separated and/or preconcentrated prior to analysis (e.g., by use of any useful chromatographic methods, such as gas chromatography (GC)). Exemplary analysis methodologies include mass spectrometry (MS), including gas chromatography-mass spectrometry (GC-MS), proton transfer reaction-mass spectrometry (PTR-MS), quadrupole mass spectrometry (QMS), or time-of-flight mass spectrometry (TOF MS); electron capture detection (ECD); flame ionization detection (FID); flame photometric detection (FPD); pulsed discharge helium ionization detection (PDHID); photoionization detection (PID); thermal conductivity detection (TCD); surface acoustic wave (SAW) detection; etc. In some embodiments, the detection includes capture of VOCs by using one or more SPME fibers and analysis with GC-MS.

Figure 2A:
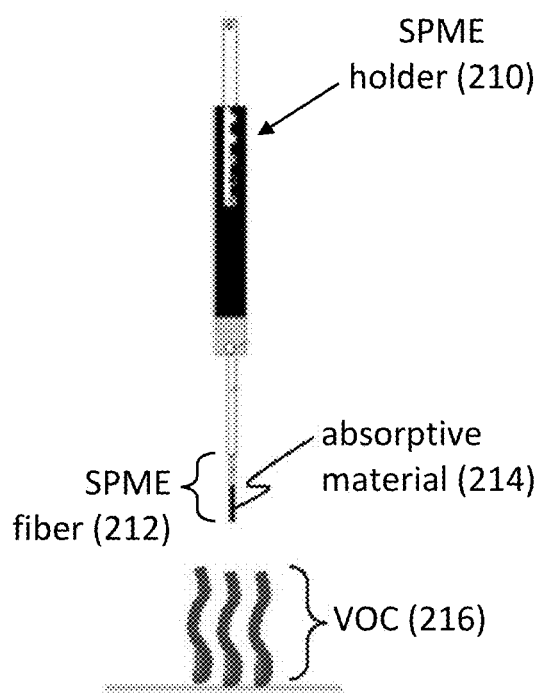
FIGS. 2A-2B show exemplary methodologies for detecting VOCs. Provided are (A) an exemplary schematic of capturing VOCs 216 on an absorptive material 214, such as that on a solid-phase microextraction (SPME) fiber 212; and (B) an exemplary schematic of capturing and detecting VOCs using SPME 222 coupled with gas chromatography-mass spectrometry (GC-MS, 232/240).
Figure 2B:
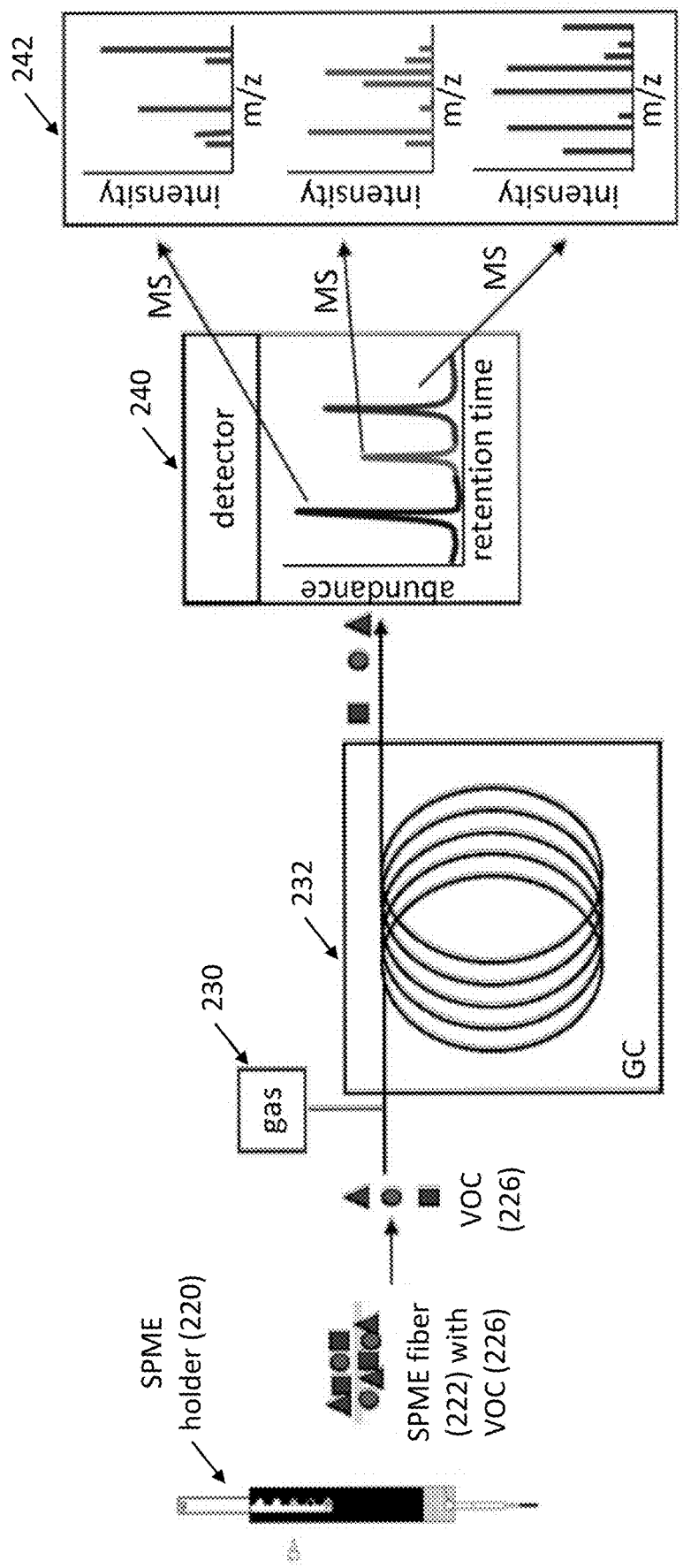

FIG. 2A provides an exemplary methodology, in which an absorptive material 214 is used to capture a VOC 216 from a sample. In particular embodiments, the absorptive material 214 is provided as a SPME fiber 212 fitted to an SPME holder 210 for handling the fiber. Any useful absorptive material can be employed, such as a polymer (e.g., poly (dimethyl siloxane)), a molecular sieve, a solid adsorbent (e.g., divinylbenzene polymer, porous carbon, etc.), as well as combinations thereof. Upon capture, the VOCs can be analyzed in any useful manner (e.g., any analysis methodologies described herein). As seen in FIG. 2B, exemplary detecting methods can include capture of one or more VOCs 226 (e.g., using an SPME fiber 222 disposed on a holder 220), releasing such VOCs 226 (e.g., by way of gas chromatography 232 employing a gas source 230) to a detector (e.g., a mass spectrometer 240), and analyzing the VOCs (e.g., by use chromatograms 242) to determine its chemical identity (e.g., as a carotenoid).

Upon detecting crop damage within a culture (e.g., employing any methods herein), any useful investigation and/or remediation steps can be conducted. In one instance, the method can include re-testing a sample obtained from the headspace of the culture. In another instance, the method can include testing a first sample obtained from the headspace of the culture and then testing a second sample that is obtained subsequent to the first sample. In yet another instance, the method can include providing one or more additives (e.g., any described herein) to protect the algal culture. Additional details are described herein.

Carotenoids, Including Oxidized Carotenoids

The present disclosure relates to the detection of a VOC to determine the presence of crop damage. Exemplary VOCs include carotenoids, as well as oxidized forms or derived forms thereof, such as terpenoids, norterpenoids, terpenes, isoprenes, monoterpenes, norisoprenoids, norcarotenoids, ionones (e.g., α-ionone, β-ionone, or γ-ionone), damascones (e.g., α-damascone, β-damascone, or γ-damascone), damascenones, and megastigmanes. Further exemplary carotenoids include β-carotene, dihydroactinidiolide, trans-β-ionone, β-cyclocitral (or 2,6,6-trimethyl-1-cyclohexene-1-carboxaldehyde), 5,6-epoxy-β-ionone, α-ionone, dihydroactinidiolide, β-ionylidene-acetaldehyde, β-apo-β-carotenone, retinal, β-apo-8'-carotenal, β-apo-10'-carotenal, β-apo-12'-carotenal, β-apo-14'-carotenal, 2,2,6-trimethylcyclohexanone, 2,6,6-trimethyl-1-cyclohexene-1-acetaldehyde, 4-(2,6,6-trimethyl-1-cyclohexen-1-yl)-2-butanone, $C_{14}$-dialdehyde, 1-(4-methylphenyl)-ethenone, 4-methylene-2,8,8-trimethyl-2-vinyl-bicyclo[5.2.0]nonane, 3-ethylcyclohexene, heptadecane (e.g., 8-heptadecene), 3-hexen-1-ol, isoprene, and (E,E)-1,3,5-undecatriene. Yet other carotenoids are described in Achyuthan K E et al., "Volatile metabolites emission by in vivo microalgae—an overlooked opportunity?," *Metabolites* 2017; 7:39 (46 pp.) and Winterhalter P & Rouseff R (eds.), "Chapter 1, Carotenoid-derived aroma compounds: an introduction," ACS, Washington, DC (2002), pp. 1-17, each of which is incorporated herein by reference in its entirety.

In one embodiment, the carotenoid has a structure of formula (I):

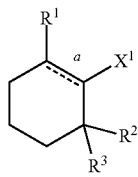

(I)

or a salt thereof, wherein:
each of $R^1$, $R^2$, and $R^3$ is, independently, H, optionally substituted alkyl (e.g., $C_{1-12}$ alkyl), or optionally substituted alkenyl (e.g., optionally substituted $C_{2-12}$ alkenyl);
$X^1$ is H, oxo, optionally substituted alkyl (e.g., optionally substituted $C_{1-24}$ alkyl, including an optionally substituted $C_{1-24}$ or $C_{2-24}$ alkyl having one or more oxo), optionally substituted alkenyl (e.g., optionally substituted $C_{2-24}$ alkenyl, including an optionally substituted $C_{2-24}$ alkenyl having one or more oxo), or optionally substituted acyl (e.g., optionally substituted $C_{1-24}$ acyl); and
the dashed double bond indicated at position a may be present or absent.

In some embodiments, $X^1$ is optionally substituted alkenyl (e.g., optionally substituted $C_{2-24}$ alkenyl). In particular embodiments, $X^1$ is optionally substituted $C_{2-24}$ alkenyl having one or more oxo. In other embodiments, $X^1$ is optionally substituted alkyl (e.g., optionally substituted $C_{1-24}$ alkyl). In yet other embodiments, $X^1$ is optionally substituted $C_{1-24}$ alkyl having one or more oxo.

In another embodiment, the carotenoid has a structure of formula (II):

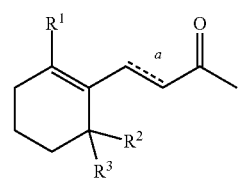

(II)

or a salt thereof, wherein:
each of $R^1$, $R^2$, and $R^3$ is, independently, H, optionally substituted alkyl (e.g., $C_{1-12}$ alkyl), or optionally substituted alkenyl (e.g., optionally substituted $C_{2-12}$ alkenyl); and
the dashed double bond indicated at position a may be present or absent.

In any embodiment of the carotenoid having the structure of formula (I) or (II), each of $R^1$, $R^2$, and $R^3$ is, independently, optionally substituted alkyl (e.g., $C_{1-12}$ alkyl).

In some embodiments, the carotenoid is an oxidized form of a compound having the structure of formula (IIIa) or (IIIb):

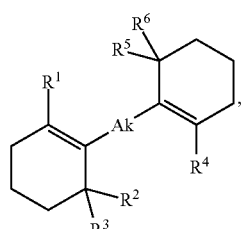

(IIIa)

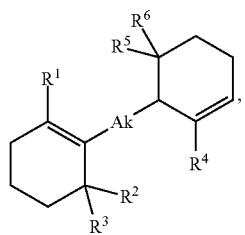

(IIIb)

or a salt thereof, wherein:
each of $R^1$, $R^2$, $R^3$, $R^4$, $R^5$, and $R^6$ is, independently, H, optionally substituted alkyl (e.g., $C_{1-12}$ alkyl), or optionally substituted alkenyl (e.g., optionally substituted $C_{2-12}$ alkenyl); and Ak is optionally substituted alkylene (e.g., optionally substituted $C_{1-24}$ alkylene) or optionally substituted alkenylene (e.g., optionally substituted $C_{2-24}$ alkenylene).

In other embodiments, the carotenoid is an oxidized form of a compound having the structure of formula (IV):

Cy-Ak-Cy                 (IV)

or a salt thereof, wherein:
  each Cy is, independently, optionally substituted cycloalkyl (e.g., optionally substituted $C_6$ cycloalkyl) or optionally substituted cycloalkenyl (e.g., optionally substituted $C_6$ cycloalkenyl); and
  Ak is optionally substituted alkylene (e.g., optionally substituted $C_{1-24}$ alkylene) or optionally substituted alkenylene (e.g., optionally substituted $C_{2-24}$ alkenylene).

In yet other embodiments, the carotenoid is an oxidized form of a compound having the structure of formula (V):

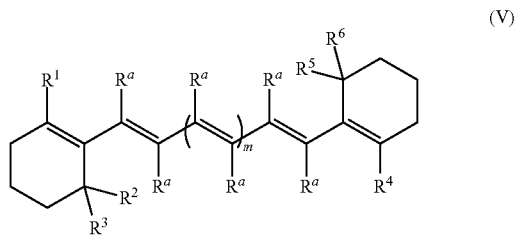

(V)

or a salt thereof, wherein:
  each of $R^1$, $R^2$, $R^3$, $R^4$, $R^5$, and $R^6$ is, independently, H, optionally substituted alkyl (e.g., $C_{1-12}$ alkyl), or optionally substituted alkenyl (e.g., optionally substituted $C_{2-12}$ alkenyl);
  each $R^a$ is, independently, H or optionally substituted alkyl (e.g., $C_{1-12}$ alkyl); and
  m is an integer of from about 1 to 24.

An oxidized form of a compound includes one or more compounds formed during enzymatic or non-enzymatic oxidative cleavage. Exemplary oxidized forms can include oxidation of one or more double bonds in the carotenoid backbone (e.g., oxidation of one or more double bonds in Ak of a compound of formula (IIIa), (IIIb), (IV), (V), or a salt thereof).

Crop Damage

Crop damage can arise from a parasite, a grazer, a pathogen (e.g., a virus, a bacterium, or a fungus), a contaminant, or other chemical compounds. Crop damage can also arise from any organism that affects the health of a culture having desired algae. Exemplary organisms include zooplankton, rotifers (e.g., *Brachionus plicatilis*), copepods (e.g., *Calanus*), other algae (e.g., golden algae or chrysophytes), chytrids, bacteria (e.g., *Vampirovibrio chlorellavoras*), virus (e.g., chlorovirus), dinoflagellates (e.g., *Oxyrrhis marina*), etc. Examples of desired algae within a culture include any useful for production of biofuels. Exemplary desired algae include microalgae, such as *Arthrospira*, *Dunaliella* (e.g., *D. salina*), *Microchloropsis* (e.g., *M. salina* or *M. gaditana*), *Phaeodactylum* (e.g., *P. tricornutum*), etc.

Algal Culture Additives

Algal cultures may benefit from the use of one or more additives. Such additives may be employed to protect crops from damage and/or pond crashes. Non-limiting exemplary additives include one or more bacteria (e.g., Alphaproteobacteria (e.g., Rhodobacteraceae, including *Roseobacter*, *Ruegeria, Paracoccus,* and *Phenylobacterium*), Actinobacteria (e.g., *Dietzia*), Cytophagia (e.g., *Marinoscillum*), and Gammaproteobacteria (e.g., *Marinobacter, Pseudomonas, Alteromonas,* and *Methylophaga*); one or more pesticides or biocides (e.g., rotenone or tossendanin); and one or more chemical agents (e.g., quinine, quinine sulfate, formaldehyde, ammonia, an oxidant (e.g., hydrogen peroxide, hypochlorite, etc.), copper, etc., as well as salts of any of these)). Further additives are described in Fisher C L et al., "Bacterial communities protect the alga *Microchloropsis salina* from grazing by the rotifer *Brachionus plicatilis*," *Algal Res.* 2019; 40:101500 (9 pp.); Van Ginkel S W et al., "Taking advantage of rotifer sensitivity to rotenone to prevent pond crashes for alga-biofuel production," *Algal Res.* 2015; 10:100-3; and Wang H et al., "The contamination and control of biological pollutants in mass cultivation of microalgae," *Bioresour. Technol.* 2013; 6:745-50, each of which is incorporated herein by reference in its entirety.

EXAMPLES

Example 1: Chemical Profiling of Volatile Organic Compounds in the Headspace of Algal Cultures as Early Biomarkers of Algal Pond Crashes Algae ponds used in industrial biomass production are susceptible to pathogen or grazer infestation, resulting in pond crashes with high economic costs. Current methods to monitor and mitigate unhealthy ponds are hindered by a lack of early indicators that precede culture crash.

As the energy needs of the world increase, dependence on non-renewable sources of energy remains a concern. Increased production of corn starch or sugarcane-based ethanol has resulted in increased atmospheric carbon dioxide levels, diversion of arable land from food production, and increased consumer cost for sugar and corn.[1] For these reasons, microalgae production systems are considered a promising avenue for biofuel production.

Microalgal strains are capable of growth in a range of environments (e.g. freshwater, marine, hypersaline, highly acidic) including high-nutrient municipal wastewater systems,[2] allowing for simultaneous bioremediation and biofuel production. Microalgae's ability for rapid growth in non-potable (brackish or marine) water sources using non-arable land, combined with their high capacity for fixation of atmospheric carbon dioxide, and high lipid-to-biomass ratios are significant advantages toward its use as a biofuel feedstock. The development of optimized systems for sustainable and dependable biofuel production through algal pond systems are necessary as the global energy strategies continue to evolve.[3]

Figure 3B:
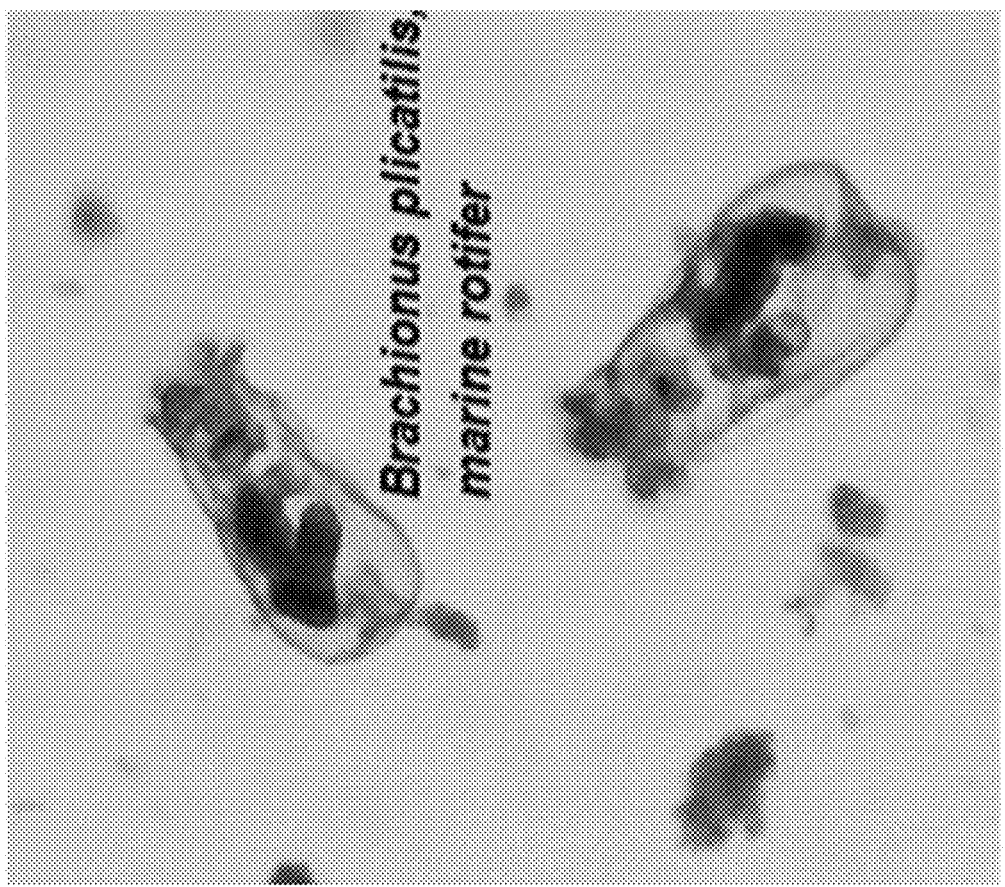
FIGS. 3A-3B show (A) 15 L algal mass cultures (analogous to production ponds) with a healthy algal culture on the left compared with a crashed algal culture on the right; and (B) *Brachionus plicatilis* (average length 160 μm), an exemplary marine rotifer, in a field of microalgae, *Microchloropsis salina*.
Figure 3A:
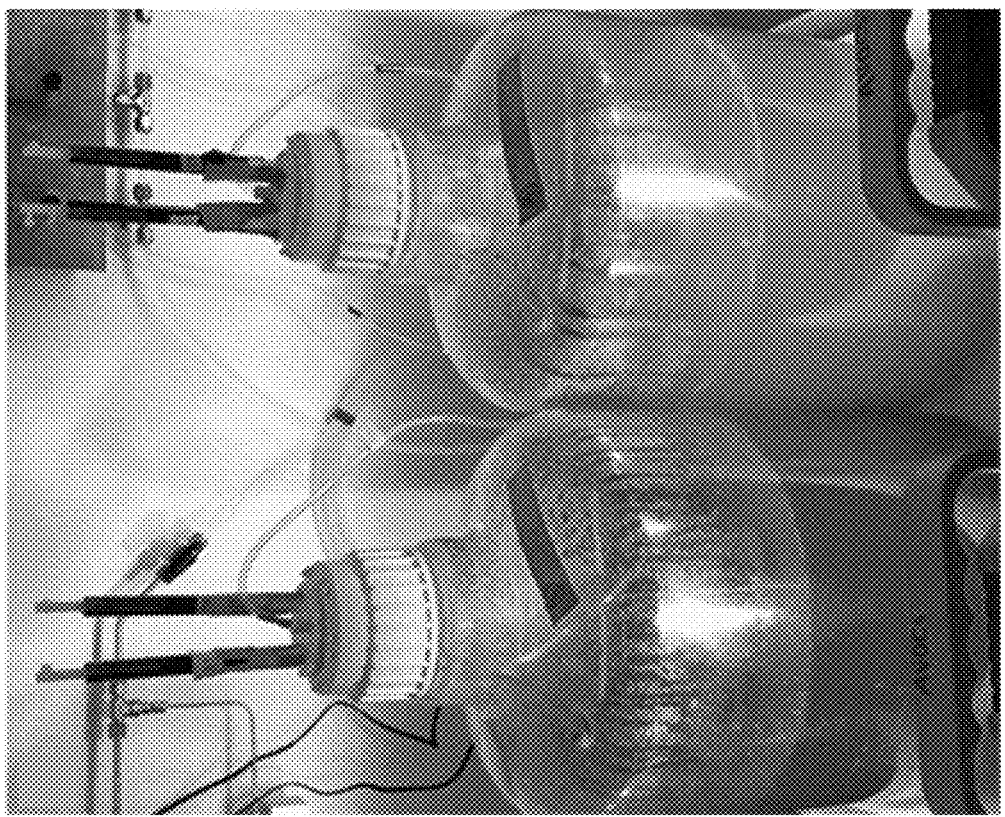

A major challenge faced in algal production are 'pond crashes', which are defined as devastating, often unpredictable losses of entire crops due to parasitism, grazing, weather, or many other factors. Closed photobioreactors are less likely to be susceptible to contamination with deleterious species (e.g. viruses, fungi, protozoans, detrimental microbes), but involve higher capital costs[4] and, once contaminated, can be difficult to disinfect. Open algal ponds are less expensive to set up but are more likely to succumb to crashes (FIG. 3A) caused by grazing or parasitism.[5, 6] Notably, a single adult marine rotifer, *Brachionus plicatilis* (FIG. 3B), can consume 200 microalgal cells per minute and double in population within 1-2 days.[7] It is estimated that pond crashes account for 30% loss of annualized algal production[4] and represent a significant economic barrier to biofuel production.[8]

Current pond crash mitigation strategies, both prophylactic and interdictive, are largely focused on chemical treatments, such as hypochlorite,[9] copper,[10, 11] quinine sulfate,[12] rotenone,[13] additives that lower pH (to less than 3.0),[14] and biocides, such as tossendanin.[15] The use of chemical countermeasures as a prophylactic strategy to prevent pond crashes is prohibitively expensive for most algal industry business models. Chemical additives can degrade from sun exposure and may need to be repeatedly added to cultures to maintain protection. In addition, frequent and repeated chemical application can be environmentally detrimental through the development of resistant pest species or through unacceptable off-target effects (e.g., pisicidal effects of rotenone). However, when applied early and in a targeted fashion after the detection of a deleterious species,[16] chemical additives can be highly effective at saving algal cultures.[43] In order to attain the production levels of 25 g m$^{-2}$ d$^{-1}$ ash free dry weight (or 2,500 gallons of biofuel per acre per year),[17] deemed necessary for economic algal biofuel production, cost-effective pond monitoring strategies are necessary to reduce culture loss and increase annualized production. Currently, algal production facilities utilize light microscopy to identify contaminants, pathogens, and competing algal strains that could lead to the demise of the desired algal strain.[18] However, microscopy is slow, labor-intensive, and requires advanced operator training for differentiating various microbiota. Alternative methods involving automated and semi-automated technologies, such as FlowCAM imaging flow-cytometry,[19, 20] polymerase chain reaction, and hybridization-based assays[21, 22] are under development to increase sensitivity and expedite analysis for daily algal culture monitoring.

Volatile organic compounds (VOCs) are carbon-containing molecules with high vapor pressures at ambient Temperatures.[23] Within the field of chemical ecology, VOCs have been identified as secondary metabolites and include, but are not limited to, pheromones, semiochemicals, odorants, and phytohormones.[24, 25] Algal VOC production has been associated with intra- and inter-species communication, allelopathy, semiochemical production, and predator deterrence.[26]

A well characterized example of an algal volatile involves conversion of nonvolatile dimethylsulfoniopropionate (DMSP) to volatile dimethyl sulfide (DMS). In intact Emiliania huxleyi cells, conversion of DMSP to DMS by the enzyme DMSP lyase is minimal. However, during algal grazing, such as by the dinoflagellate *Oxyrrhis marina*, *E. huxleyi* is disrupted, releasing DMSP. Once in solution, DMSP lyases, including those from bacteria, catalyze conversion of DMSP to DMS.[27, 28] DMS then acts not only as a deterrent against herbivory by *Oxyrrhis marina*,[29] but additionally as an attractant for other species, such as birds and fish.[30]

The aims of this study were as follows: 1) develop a methodology to detect VOCs from healthy algal cultures (e.g., *Microchloropsis salina*) as well as algal cultures in the presence of a grazer (*M. salina* cultures with marine rotifer, e.g., *Brachionus plicatilis*) and 2) evaluate whether specific VOCs could serve as early indicators of an imminent culture crash. A setup based upon solid-phase microextraction (SPME) fibers coupled with gas chromatography-mass spectrometry (GC-MS) allowed for non-invasive monitoring of volatile emissions. Compounds present during the active grazing period of rotifers on algal cultures, but not produced in healthy controls, were deemed potential biomarkers of high stress conditions. We propose that these biomarker compounds are potential diagnostic tools for chemical monitoring systems in microalgal cultivation systems to enabling the early detection of culture stress for improved algal crop production.

In particular, we used SPME coupled with GC-MS to identify volatiles emitted from healthy and rotifer infested algal cultures. After 48 hours of algal growth, marine rotifers were added to the algae cultures, and VOCs were sampled from the headspace using SPME fibers. A GC-MS approach was used in an untargeted analysis of VOCs, followed by preliminary identification. In particular, the addition of *B. plicatilis* to healthy cultures of *M. salina* resulted in decreased algal cell numbers, relative to uninfected controls, and generated carotenoids (e.g., trans-β-ionone and β-cyclocitral), which were attributed to carotenoid degradation. The abundances of the carotenoid-derived VOCs increased with rotifer consumption of algae. Our results indicate that specific VOCs released by infected algae cultures may be early indicators for impending pond crashes, providing a useful tool to monitor algal biomass production and pond crash prevention. Additional details follow.

Example 2: Experimental Methods

Axenic microalgae culture: *Microchloropsis salina* (CCMP 1776) was obtained as an axenic stock culture (as determined by the supplier) from the National Center for Marine Algae and Microbiota (NCMA at Bigelow Laboratory, ME, USA). *M. salina* cultures were grown as previously described in Fisher et al.[43] For volatilomics experiments, ESAW medium was modified to contain 7.5 mM NaNO$_3$, 0.5 mM Na$_2$PO$_4$. Algal cultures were grown in 15-L of medium in 20-L polycarbonate carboys at room temperature (RT) of ~ 22° C. with 24-h light intensity of ~200 μmol m$^{-2}$s$^{-1}$ for 5 d. Carbon dioxide gas, research purity 99.999% (Matheson Tri-Gas, NJ, USA), and research grade air (70:30 N$_2$/O$_2$), VOC Free (Matheson Tri-Gas, NJ, USA) were supplied to all samples via two mass flow controllers (one for CO$_2$ and one for air). The two mass flow controllers (Alicat, AZ, USA) were set to deliver 1% CO$_2$ (9.00 cc min$^{-1}$) and 99% air (891 cc min$^{-1}$), for a total mass flow of 900 cc min$^{-1}$ split equally across six culture vessels (150 cc min$^{-1}$ sparging rate for each sample).

Xenic marine rotifers: Lots of 10$^{-15}$×10$^6$ live, xenic, marine rotifers, *Brachionus plicatilis*, were obtained from Reed Mariculture, CA, USA, 1-2 days before each inoculation and were shipped overnight on ice. Upon arrival, *B. plicatilis* were kept at 4° C. until concentrated and inoculated into algal culture for each experiment.

Preparation of cultures: Experimental cultures were grown in 20-L polycarbonate carboys (ThermoFisher Scientific, MA USA) containing 15 L nutrient enriched ESAW medium, described above. Cultures were initially inoculated with *M. salina* culture to a final concentration of 4-5×10$^6$ cells mL$^{-1}$ in 15 L. Cultures were continuously sparged at of 150 cc min$^{-1}$ with 1% CO$_2$ in air through an air stone bubbler. After 48 hours of *M. salina* growth and acclimation to culturing conditions, 1.32×10$^6$ live rotifers (final concentration of 88 rotifers mL$^{-1}$) were added to two of the four algal cultures. *Brachionus plicatilis* were allowed to warm for 1-3 h to room temperature (22° C.), were gently concentrated using a 53 μm screen filter (Florida Aqua Farms, FL, USA) down to 100 mL of culture and rinsed twice with 200 mL of ESAW medium and resuspending in 100 mL ESAW medium. Rotifers were enumerated by direct counting using a Rafter counter.

Monitoring microalgal growth and rotifer cultures: Algal culture density was determined daily by chlorophyll fluorescence (430 nm excitation, 685 nm emission) using a Tecan i-control infinite 200Pro, version 1.11.1.0. Algal cell counts were obtained via direct enumeration with a Z2 Coulter Particle Count & Size Analyzer (Beckman Coulter, Pasadena CA) or derived by calculation via a standard curve correlating chlorophyll fluorescence with algal density. Duplicate cell counts and fluorescence measurements for each sample were averaged for each timepoint and then normalized to the final concentration measurements for the M. salina control in the absence of rotifers. Health and viability of rotifers within algal cultures was monitored daily via light microscopy. Significant differences between means of healthy or infected algal cultures were compared using two-way ANOVAs with Tukey's HSD test.

SPME headspace sampling and GC-MS data acquisition: VOCs were sampled in duplicate from the headspaces of each culture and medium control vessel using portable field sampler SPME fibers, with 65 μm polydimethylsiloxane/divinylbenzene (PDMS/DVB) coatings (Supelco, Bellefonte, PA). As two vessels were prepared for each condition, duplicate SPME samplings generated four replicate measurements. For this work, we required a "portable field sampler" fiber design to facilitate sample collection, transport, and storage over the time-course of the experiments. The bi-phasic coating (one of three commercially available field-portable options) was chosen for sampling a wide range of compounds, including polar analytes, semi-volatiles, and larger weight volatiles.

SPME samples were obtained within 1-2 hours of the fluorescence measurements that were used to determine algae concentrations. SPME exposure times were shorter for Experiment 1 (30 min) compared to Experiments 2 and 3 (60 min). SPME fibers were stored in refrigerators at 2-4° C. after sampling. Unexposed SPME fibers served as "travel blanks" to account for extraneous volatiles arising from storage conditions.

Samples were analyzed by GC-MS within 2 weeks of collection. An untargeted GC-MS approach was used to analyze the collected VOCs with an Agilent 5975 T GC-MSD (Agilent Technologies, Santa Clara, CA) using an Agilent HP-5 ms column (30 m×250 μm×0.25 μm) coupled to a single quadrupole mass analyzer with helium carrier gas at a constant flow rate of 1.2 mL/min. VOCs absorbed on the SPME fiber were desorbed in the heated GC inlet (280° C.) for 15 seconds using splitless injection. The column temperature was programmed, starting at 40° C. for 3 min, ramped at 5° C./minute from 40 to 150° C., ramped at 15° C./min from 150° C. to 280° C. and held for 2 min. The total run time was 35.67 min. Ions were generated using electron ionization (70 eV) and acquired at 4 scans/s over m/z 35-450. Data acquisition was performed under control of ChemStation software (Agilent Technologies, version E.02.02). A commercial reference of 18 standard compounds (S-22329; AccuStandard, New Haven, CT) was used to evaluate day-to-day performance and to calculate retention indices.

GC-MS data processing: After GC-MS data acquisition, data processing procedures and criteria were applied to detect and identify individual biomarkers in each condition. All ChemStation data files (consisting of biological duplicates, media controls, and unexposed fibers) were translated for compatibility with Agilent's MassHunter Software (MassHunter GC/MS Translator B.07.05). Chromatographic deconvolution and visualization were performed using MassHunter Qualitative (version B.07.00 SP2) using a Retention Time window size factor of 90.0, signal-to-noise ratio threshold of 2.00, absolute ion height filter of 1000 counts, and >5 ions required for compound detection (threshold of detection $5 \times 10^3$ counts per peak). An arbitrary small value of 1 was assigned to the signal value for compounds that were not detected.

Detected peaks were transferred into Mass Profiler Professional (MPP) 12.6.1 software and aligned across all samples in the data set using a retention time tolerance of 0.15 minutes, mass spectral match factor of 0.6 (of maximum 1.0), and a delta m/z tolerance of 0.2 Da. Putative identification of the aligned compounds was performed by searching spectra against the National Institute of Standards and Technology (NIST) mass spectral database, NIST14. Compounds with mass spectral matches >70% were subsequently annotated as the best match. Compounds that did not exceed the mass spectral match threshold were annotated using the base peak m/z and retention index (e.g. "Unknown m/z ##_RI ####").

Two criteria were used to identify volatile biomarkers unique to the Algae or Algae+Rotifer conditions: (1) detection of the biomarker in at least three of the four replicates at each sampled timepoint; and (2) a) the biomarker was present in the Algae or Algae+Rotifer condition and absent in the media blank or travel blank conditions; OR b) the biomarker was present in the Algae or Algae+Rotifer conditions at an abundance greater than 10× the abundance in the media blank or travel blank. The peak areas of potential biomarkers passing the filter criteria were compared across the three performed experiments, with regards to both individual biomarkers and groups of biomarkers belonging to the same compound class. The presence or absence of these biomarkers in each experiment was determined, and the calculated peak areas were compared to algal density measurements.

Example 3: Cell Counts of Infected and Control Cultures

Figure 4:
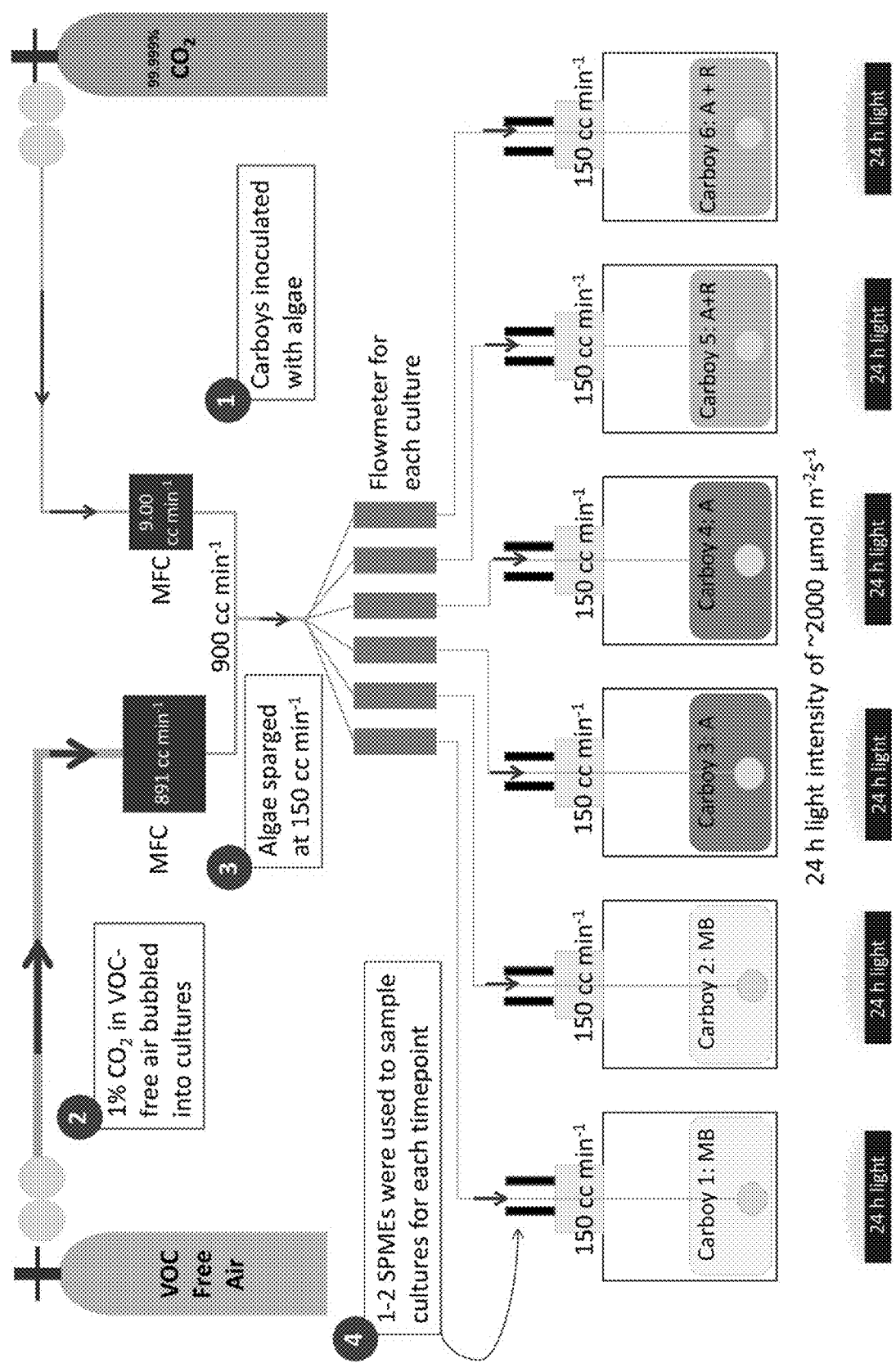
FIG. 4 shows an exemplary schematic of experimental setup for growth of *M. salina* (Algae, indicated as "A") in the presence of *B. plicatilis* (Rotifer, indicated as "R") for 5 days. Mass flow controllers (MFCs) mixed 1% $CO_2$ with VOC-free air to sparge 15 L cultures at 150 cc min$^{-1}$. One to two SPME fibers were used to sample the headspace of media blank (indicated as "MB"), Algae only (indicated as "A"), and Algae+Rotifer (indicated as "A+R") carboys for 30-60 minutes each at various timepoints over 2 to 4 days.
Figure 5:
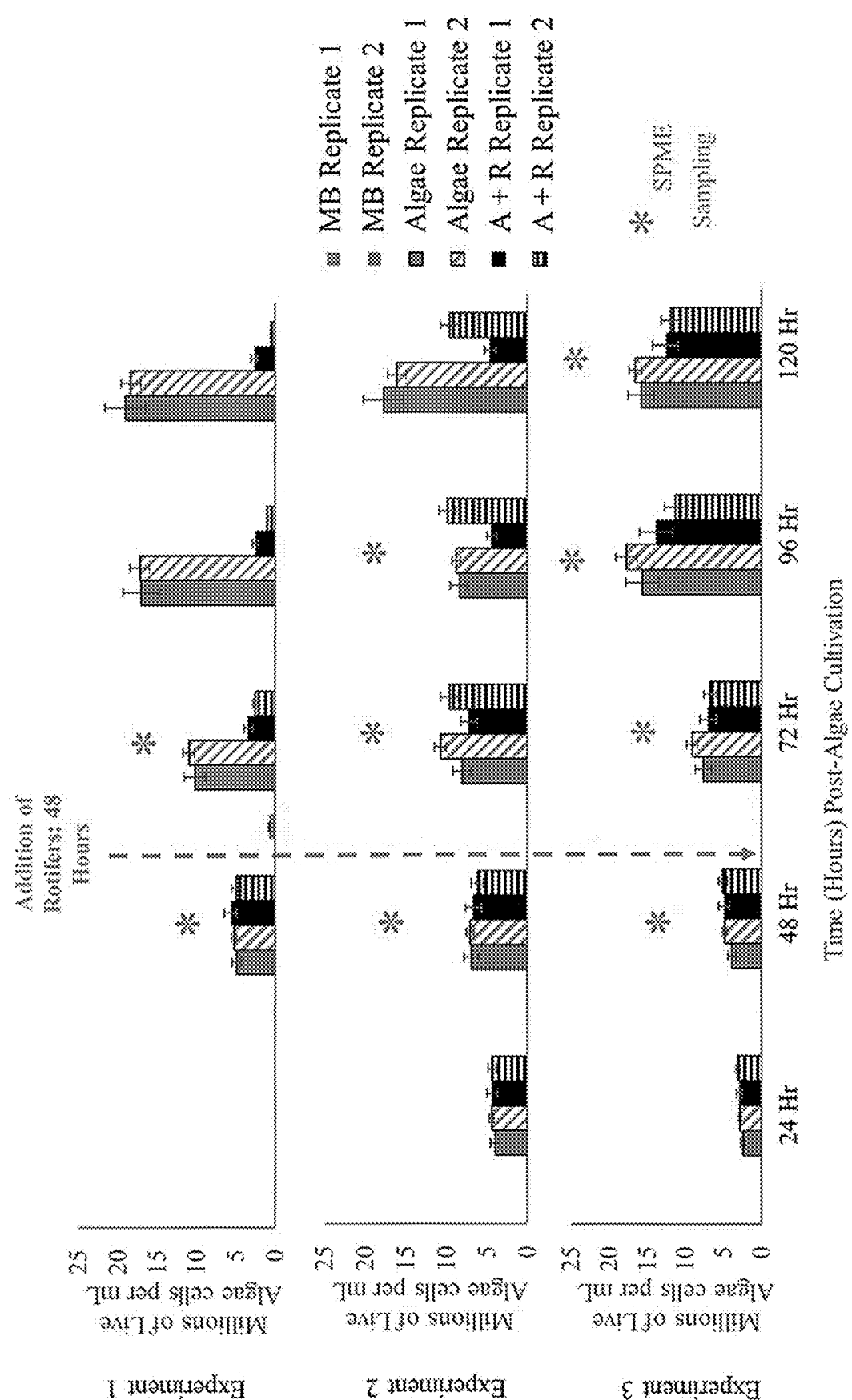
FIG. 5 shows algae concentration as determined by fluorescence measurements collected for three experiments. Similar coloring and patterns represent biological replicates of each condition: media blanks (indicated as "MB"), Algae (indicated as "A"), and Algae+Rotifer (indicated as "A+R") cultures. Error bars represent standard deviation derived from duplicate measurements for each sample. Significance levels for conditions that exhibited $p<0.05$ are also described herein in Table 1. Asterisks (*) indicate the time points for headspace VOC sampling by SPME fibers.
Figure 6A:
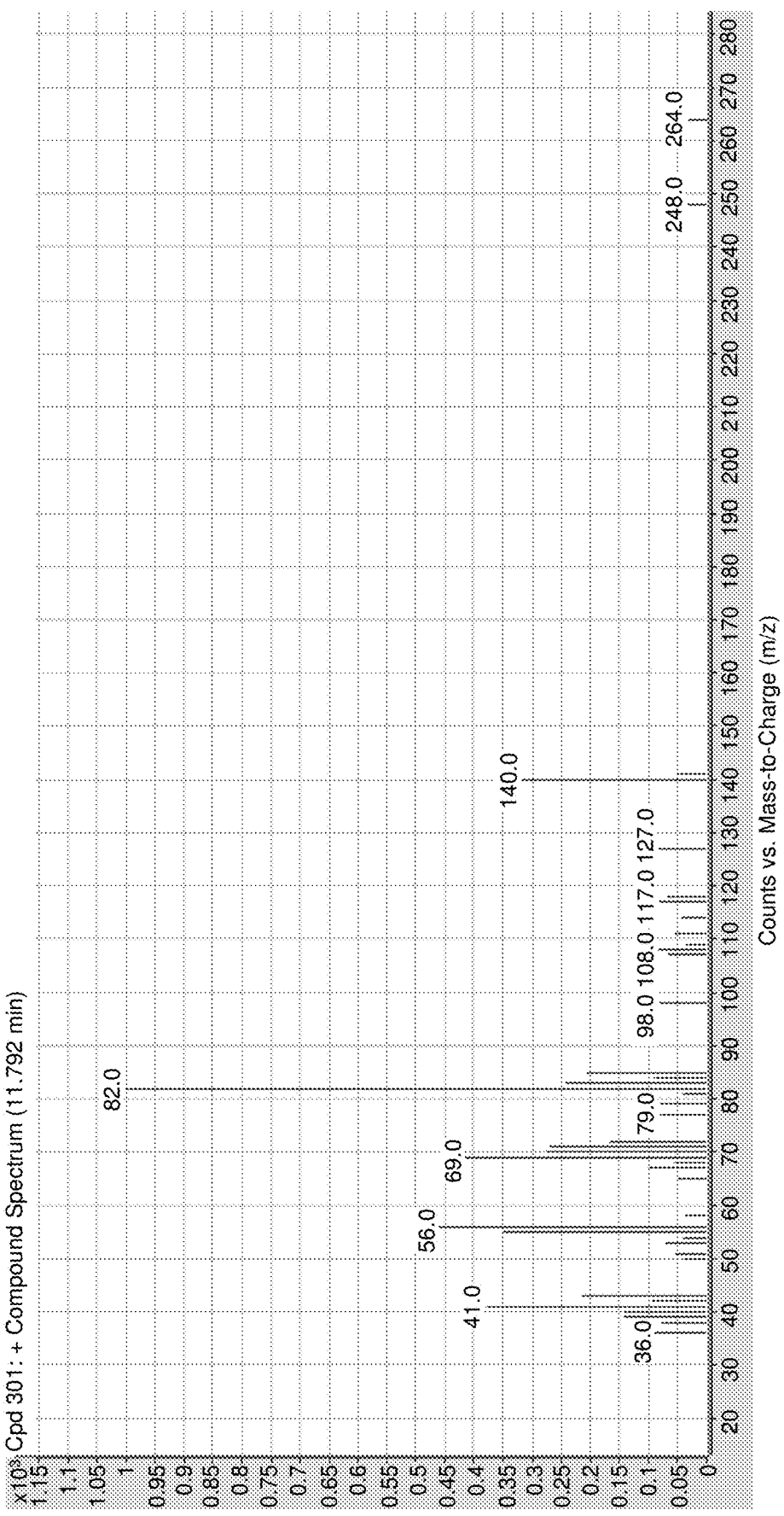
FIGS. 6A-6N show experimental mass spectra for various compounds, including (A) Compound 1, 2,2,6-trimethylcyclohexanone; (B) Compound 2; (C) Compound 3; (D) Compound 4, β-cyclocitral; (E) Compound 5, 4-(2,6,6-trimethyl-1-cyclohexen-1-yl)-2-butanone; (F) Compound 6, trans-β-ionone; (G) Compound 7; (H) Compound 8; (I) Compound 9, methyl ester 3-nonenoic acid; (J) Compound 10; (K) Compound 11; (L) Compound 12; (M) Compound 13, hexadecenoic acid; and (N) Compound 14, in which compound names or m/z (mass/charge) and retention index (RI) are also provided.
Figure 6B:
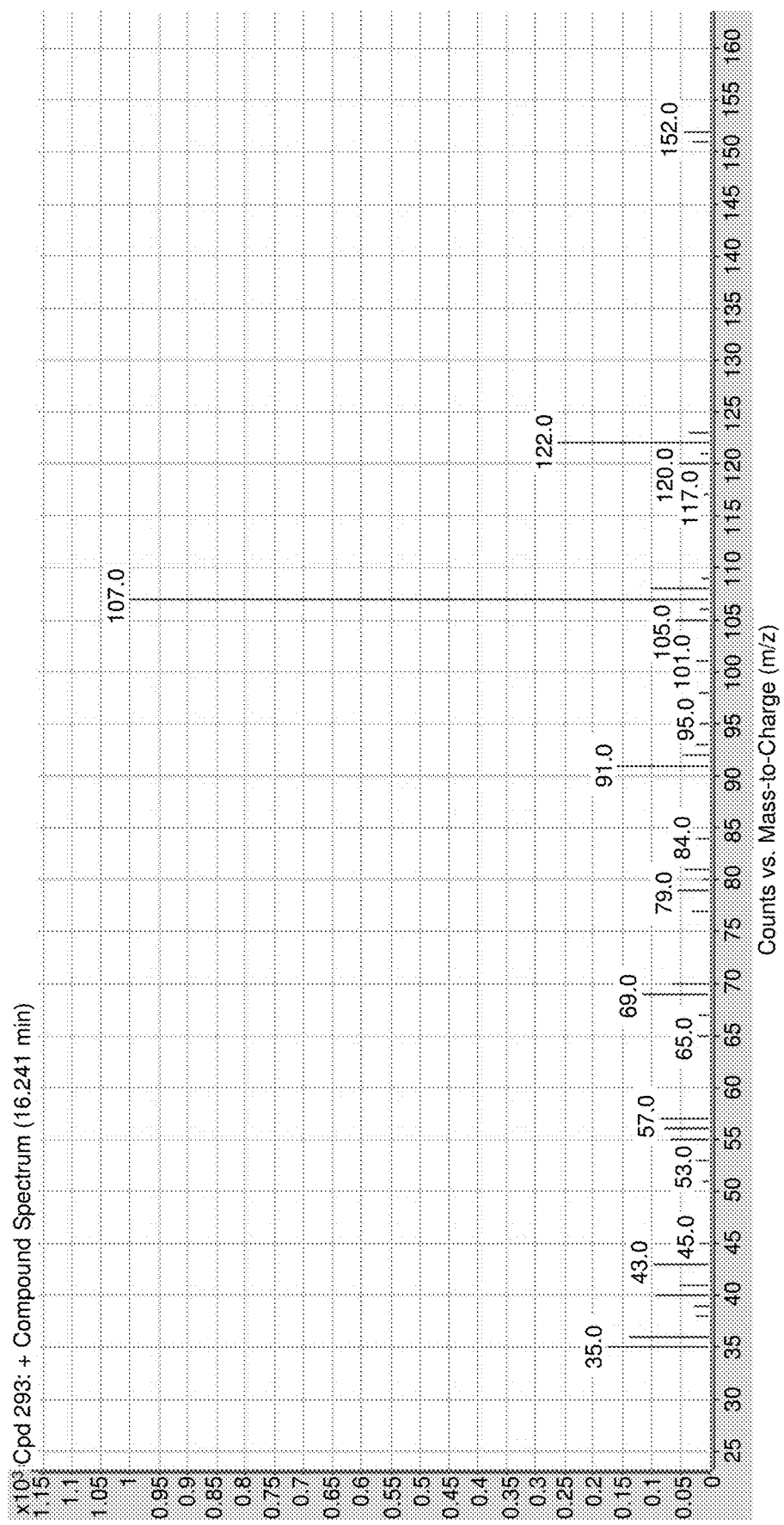
Figure 6C:
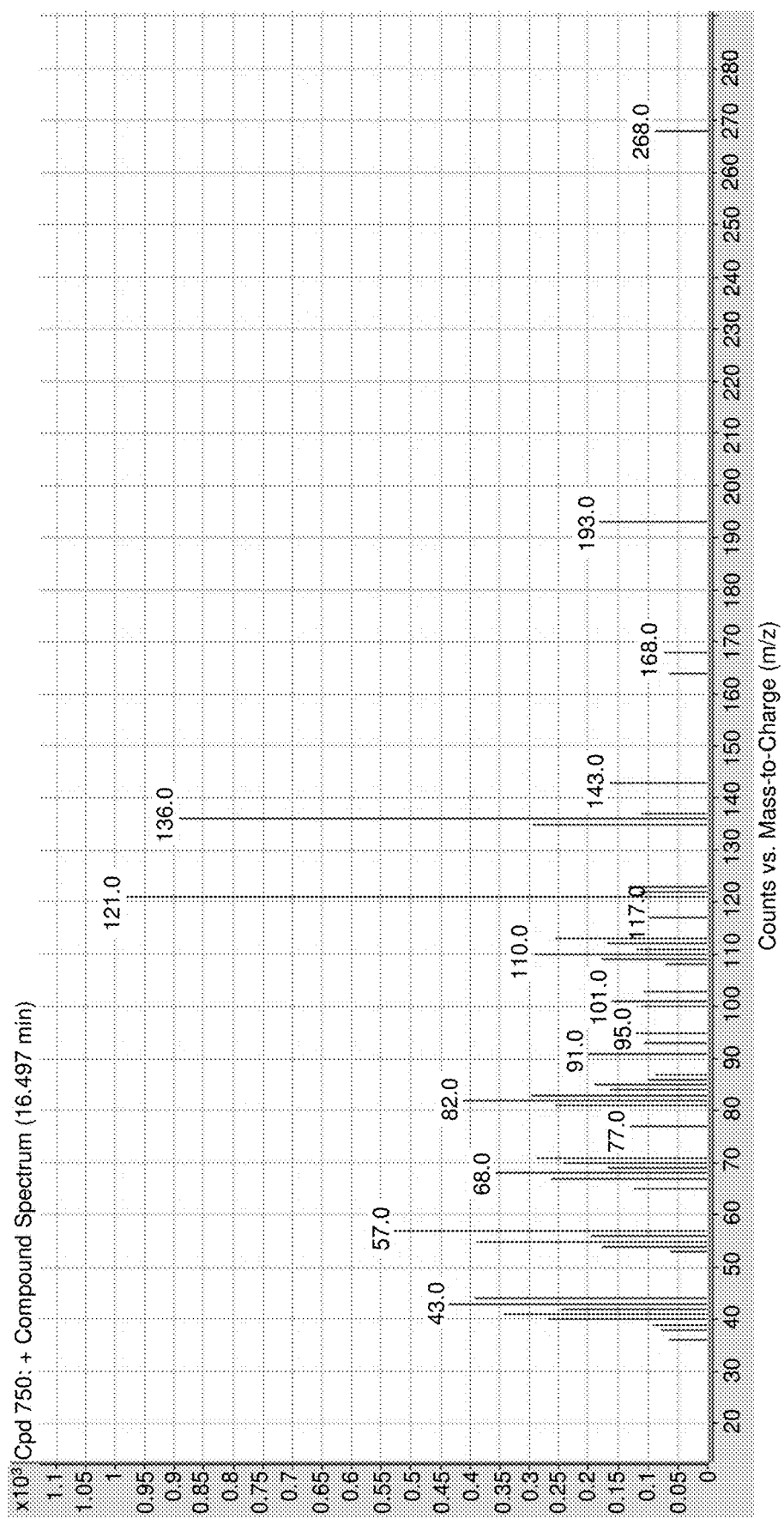
Figure 6D:
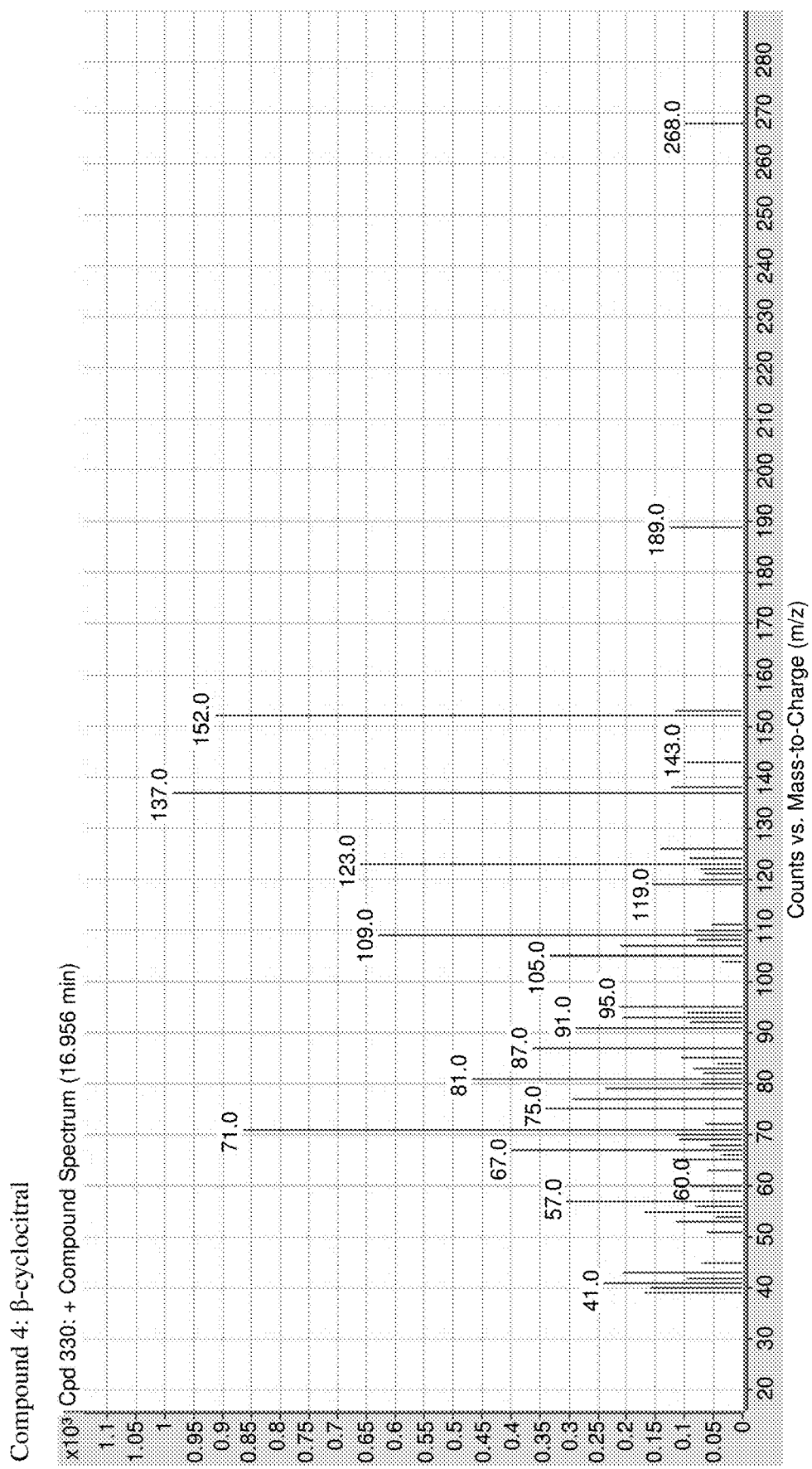
Figure 6E:
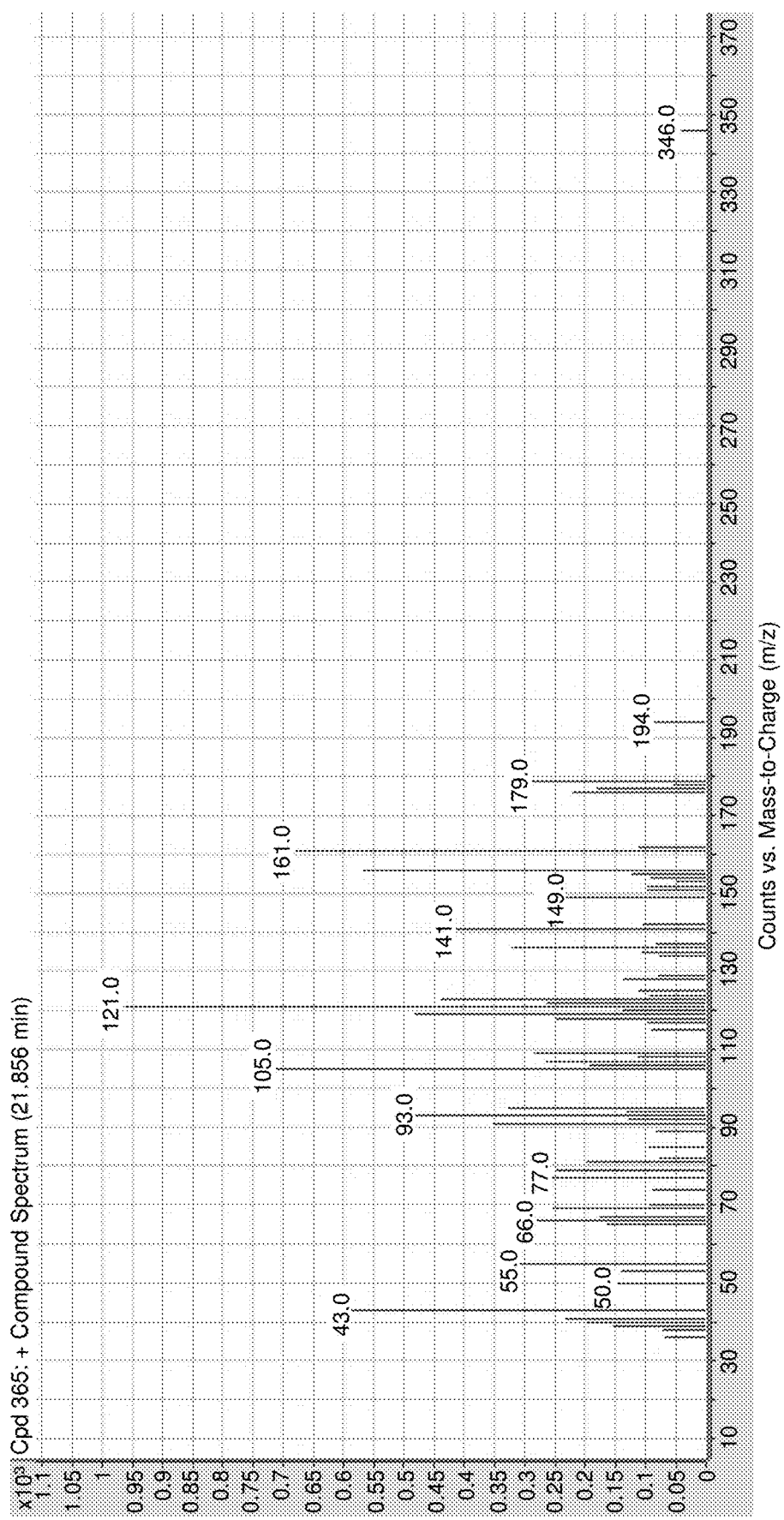
Figure 6F:
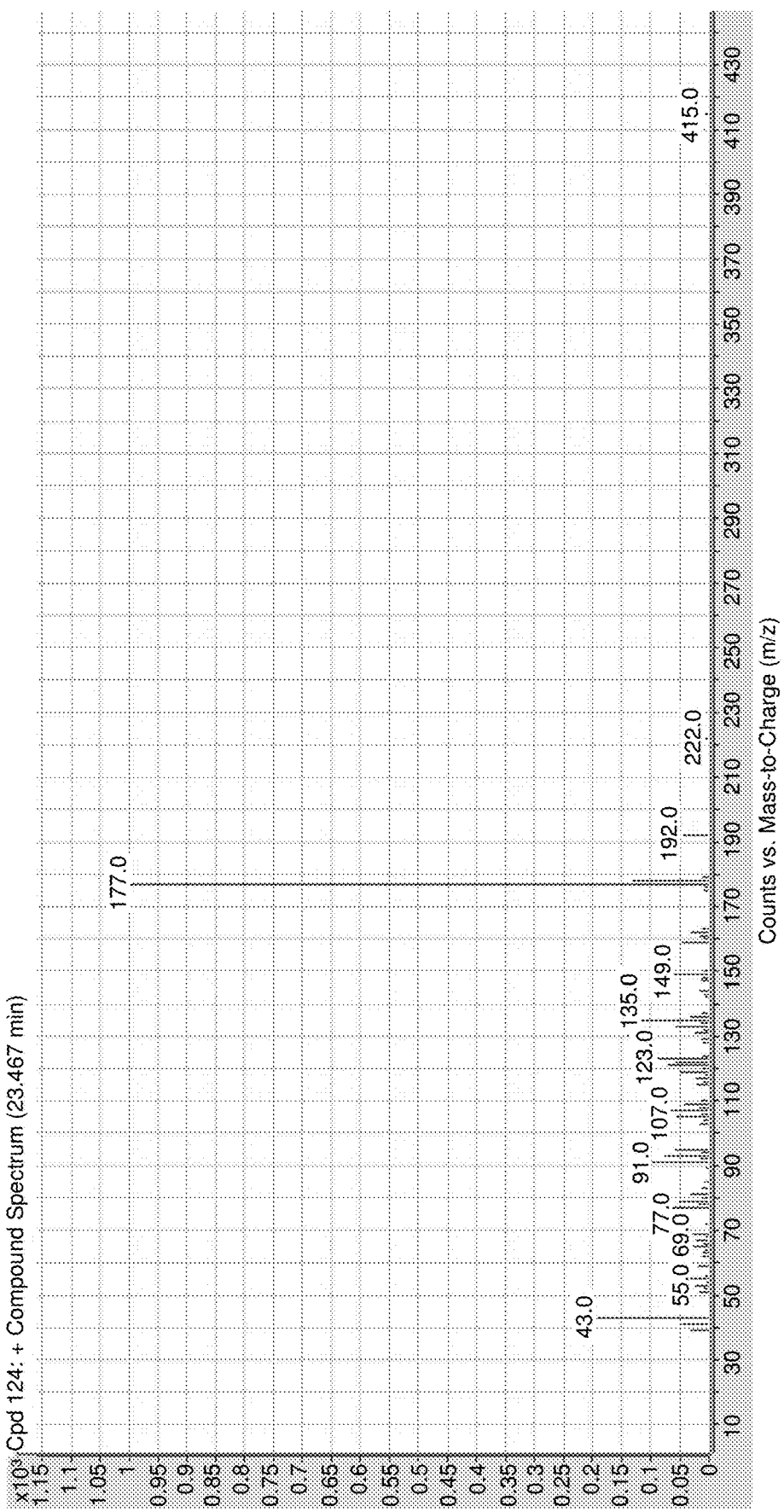
Figure 6G:
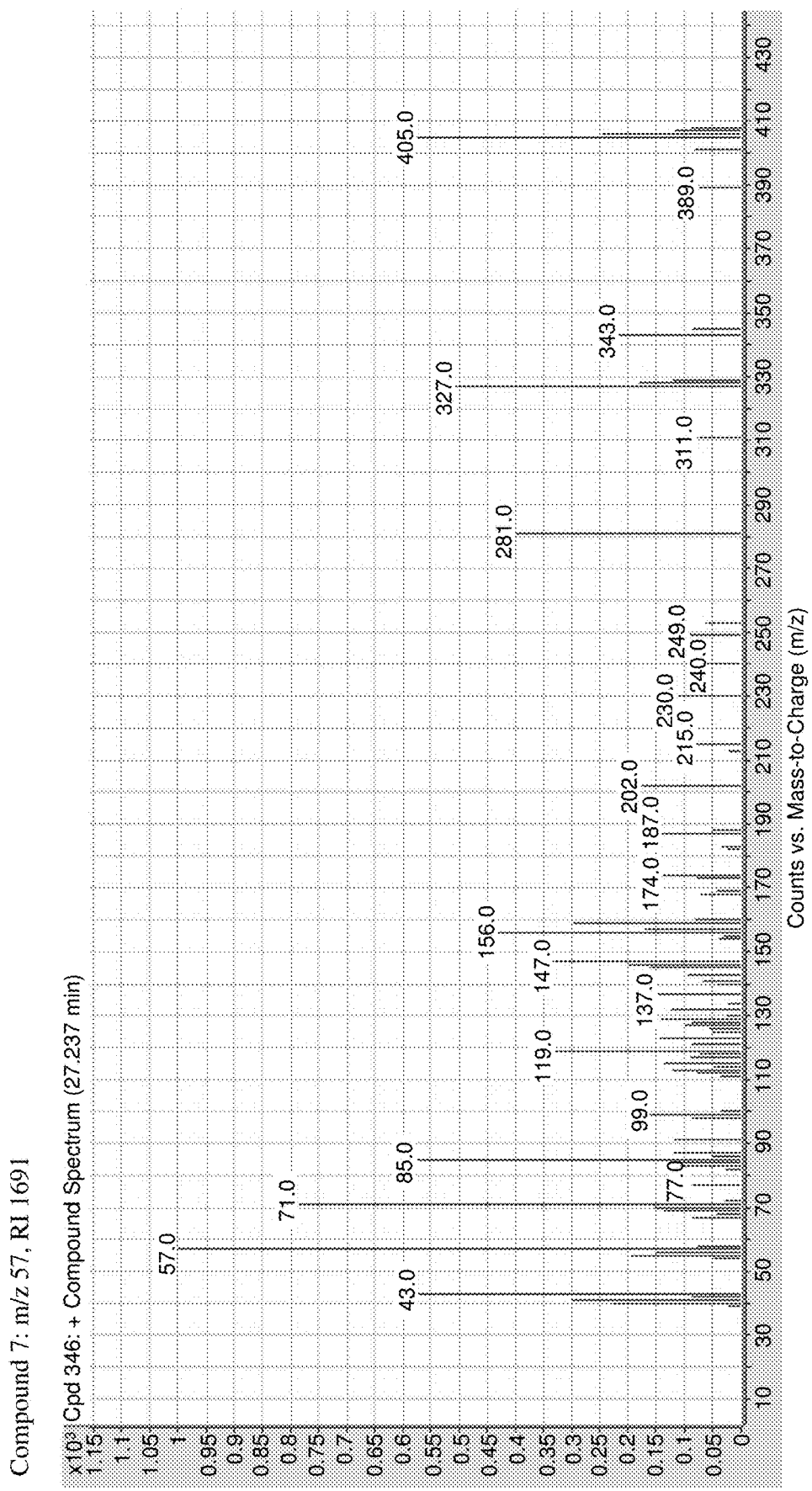
Figure 6H:
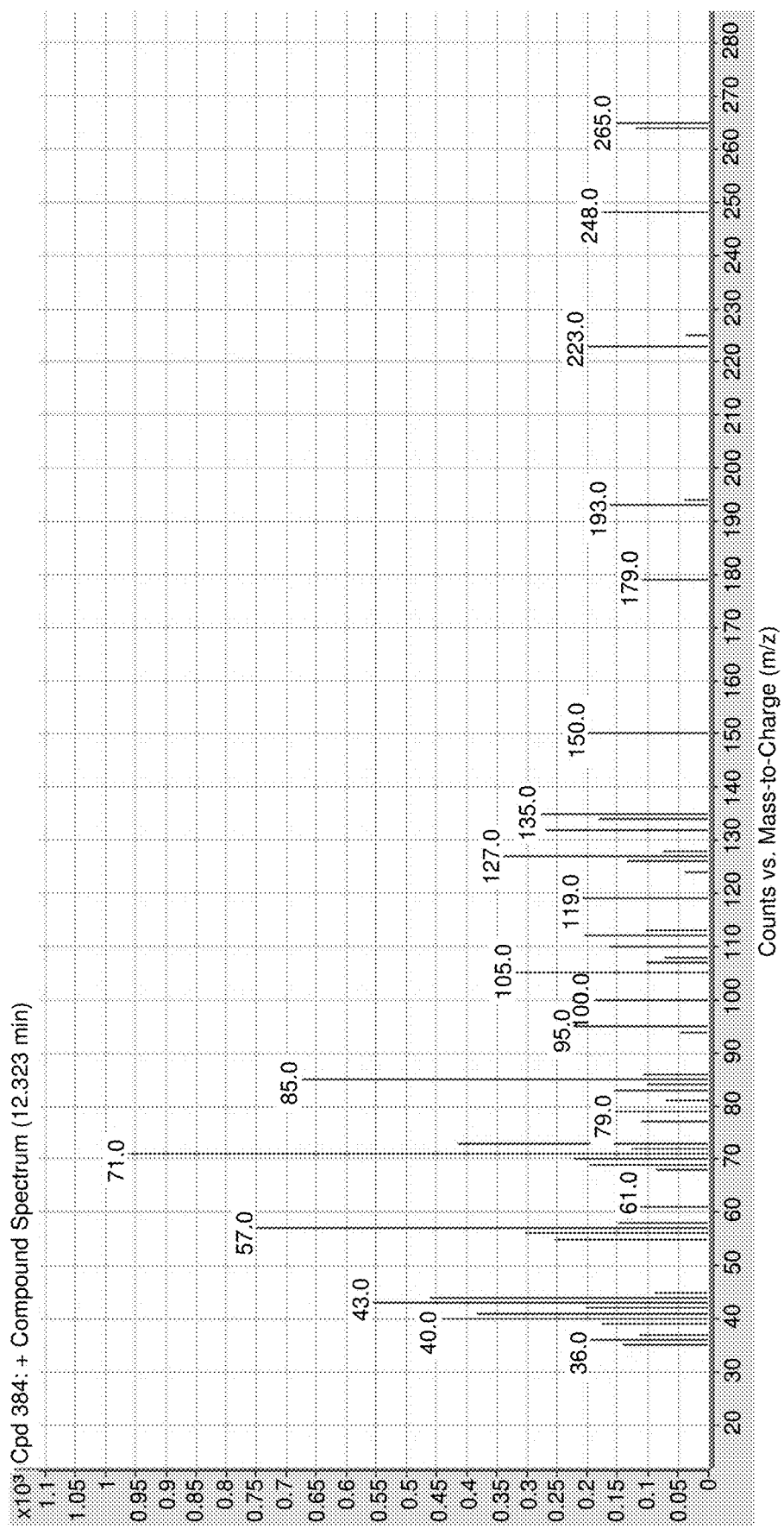
Figure 6I:
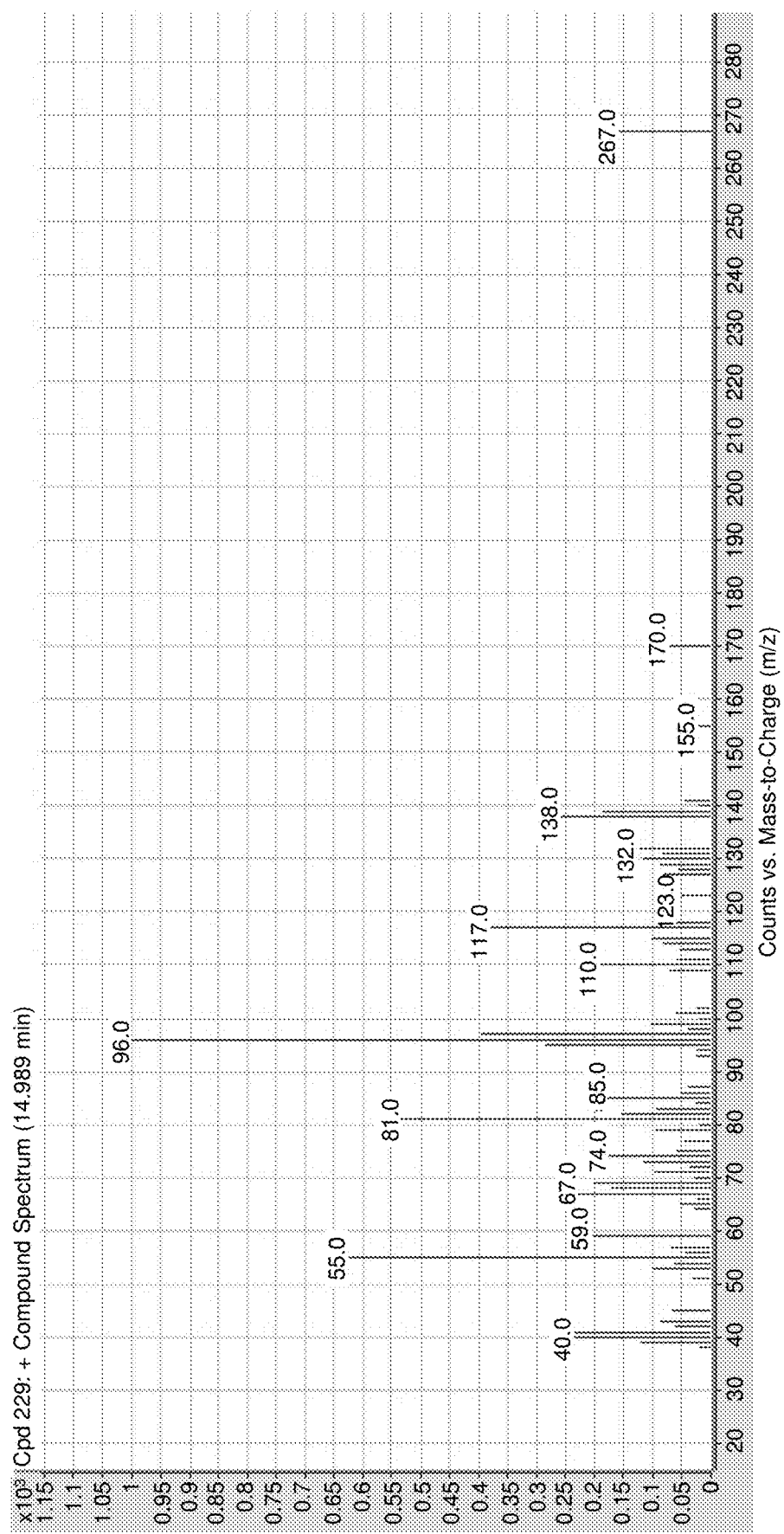
Figure 6J:
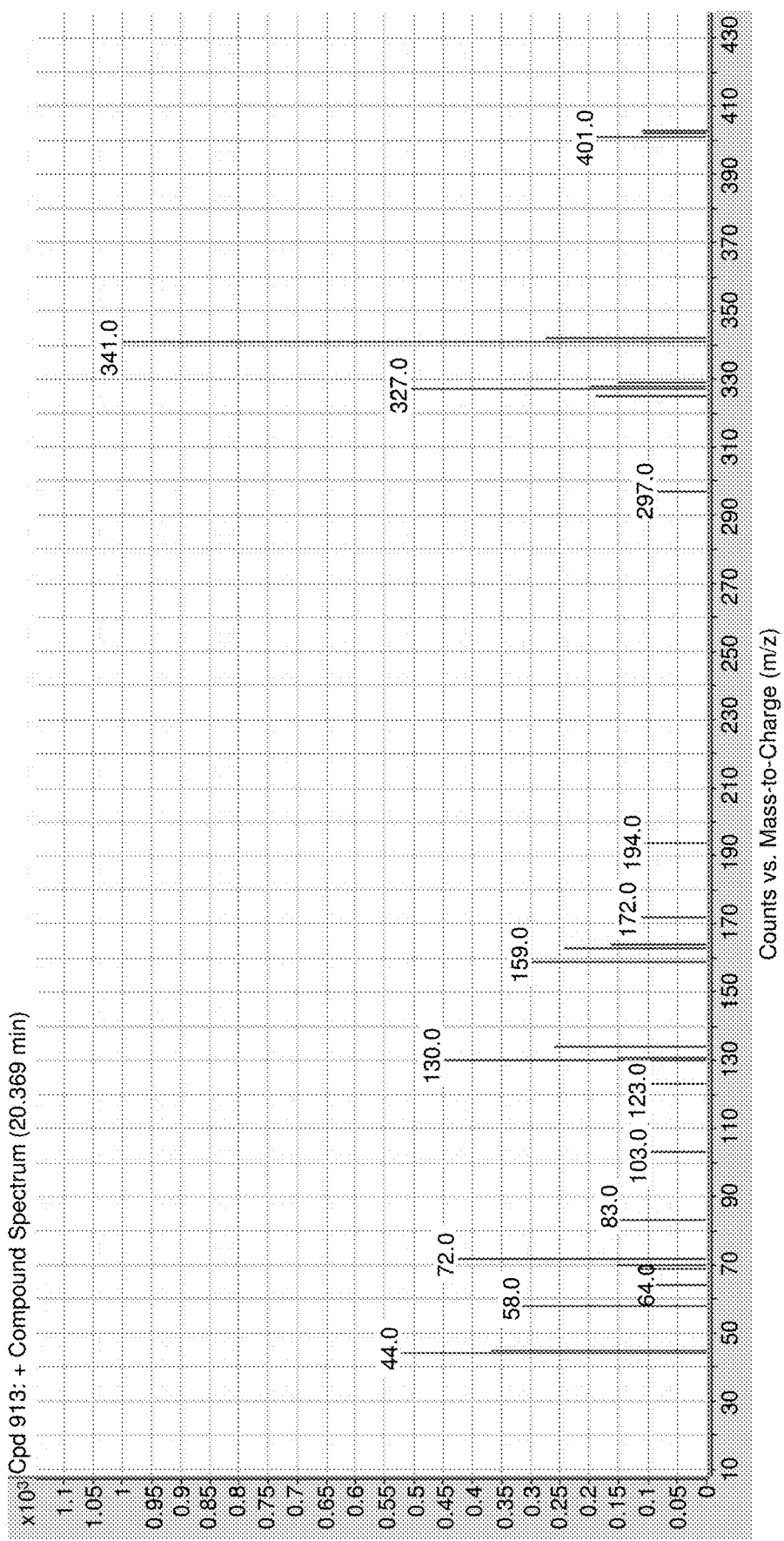
Figure 6K:
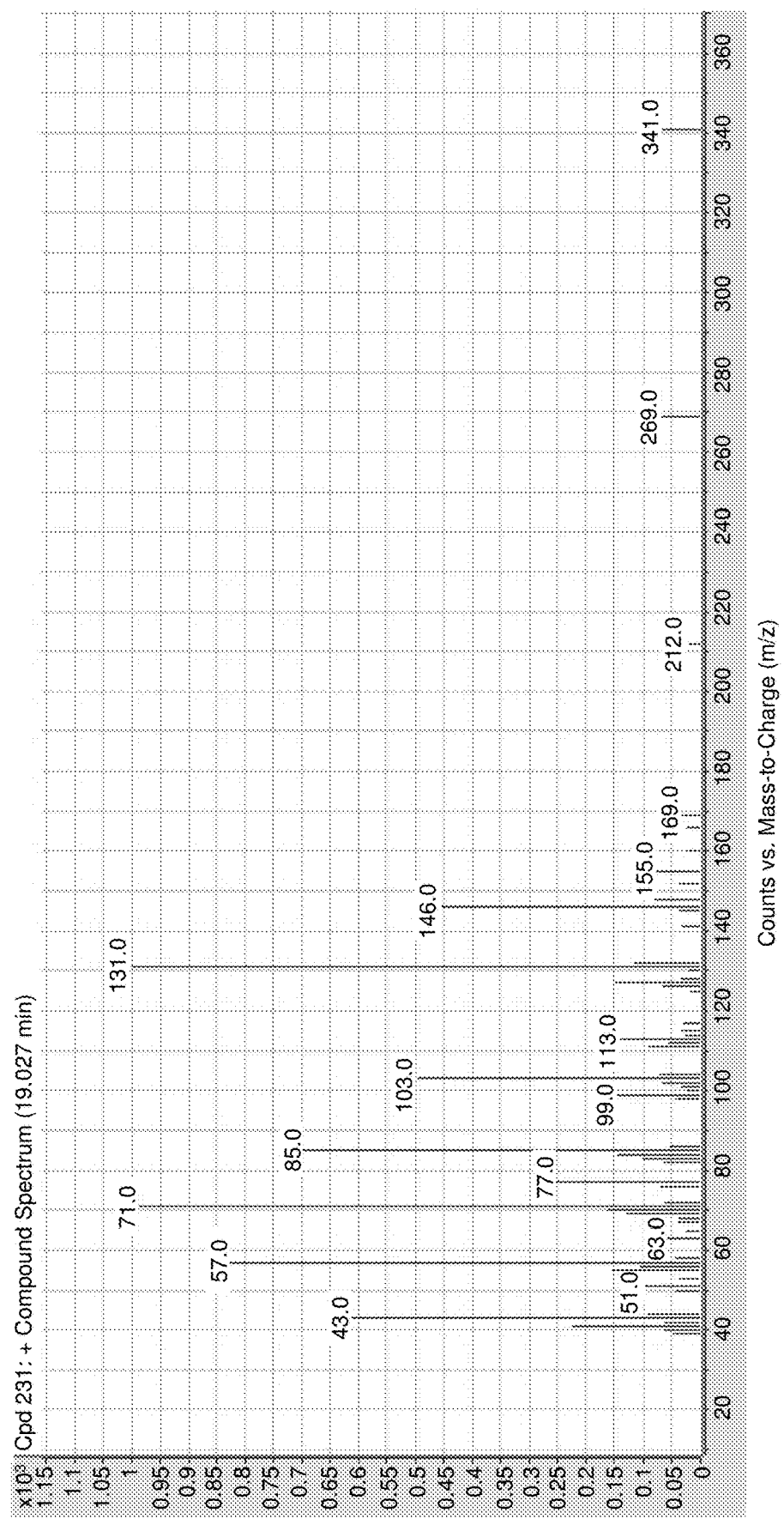
Figure 6L:
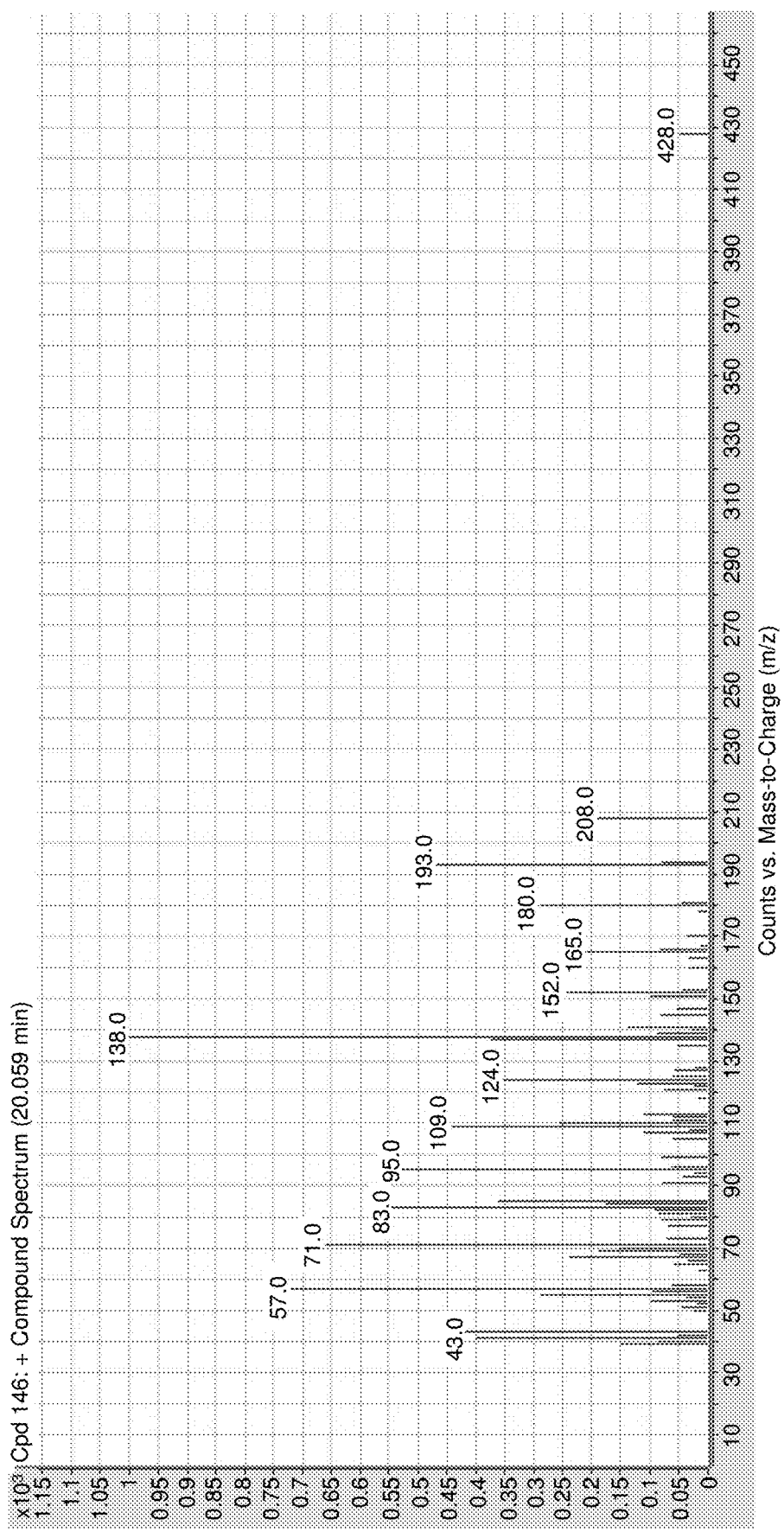
Figure 6M:
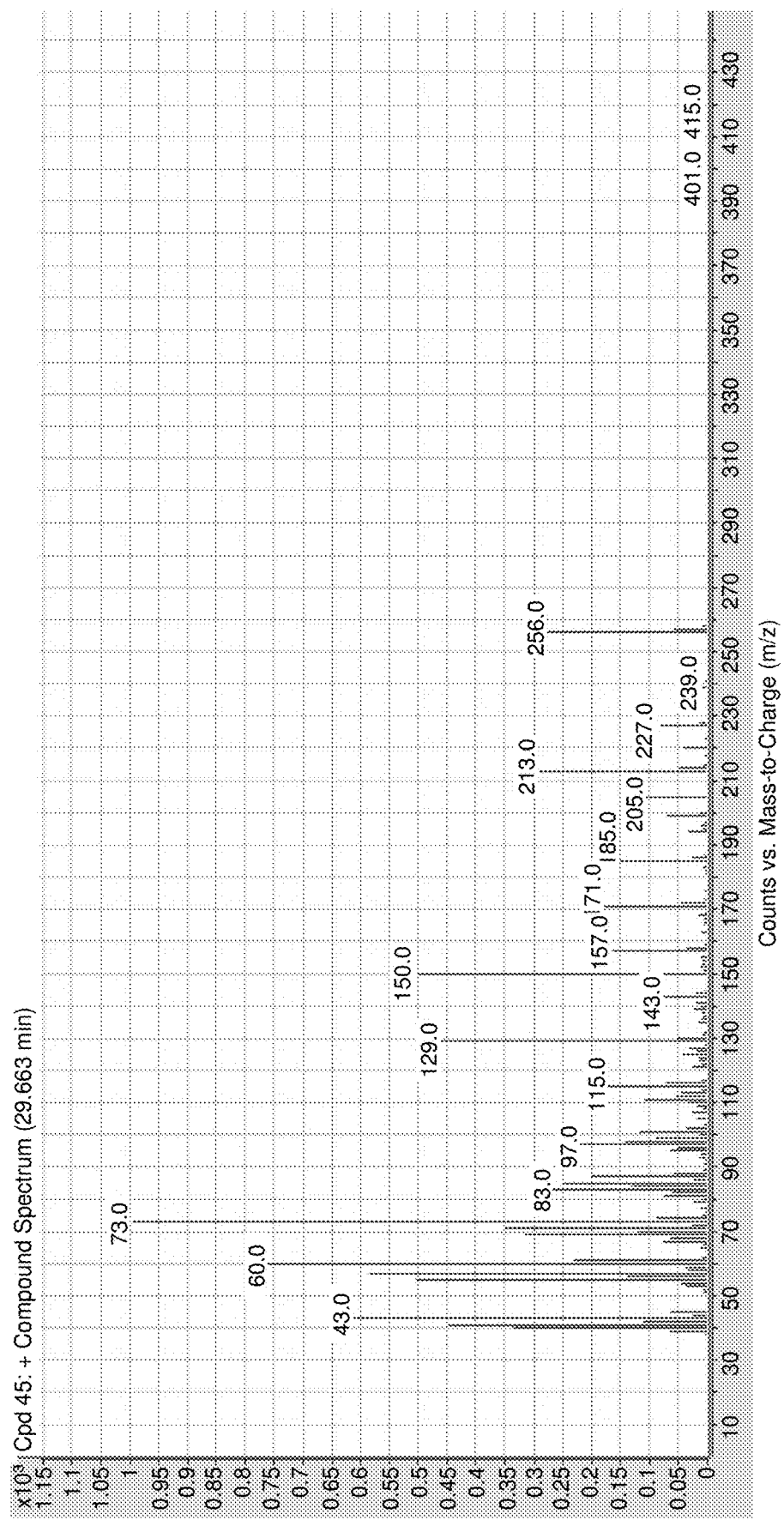
Figure 6N:
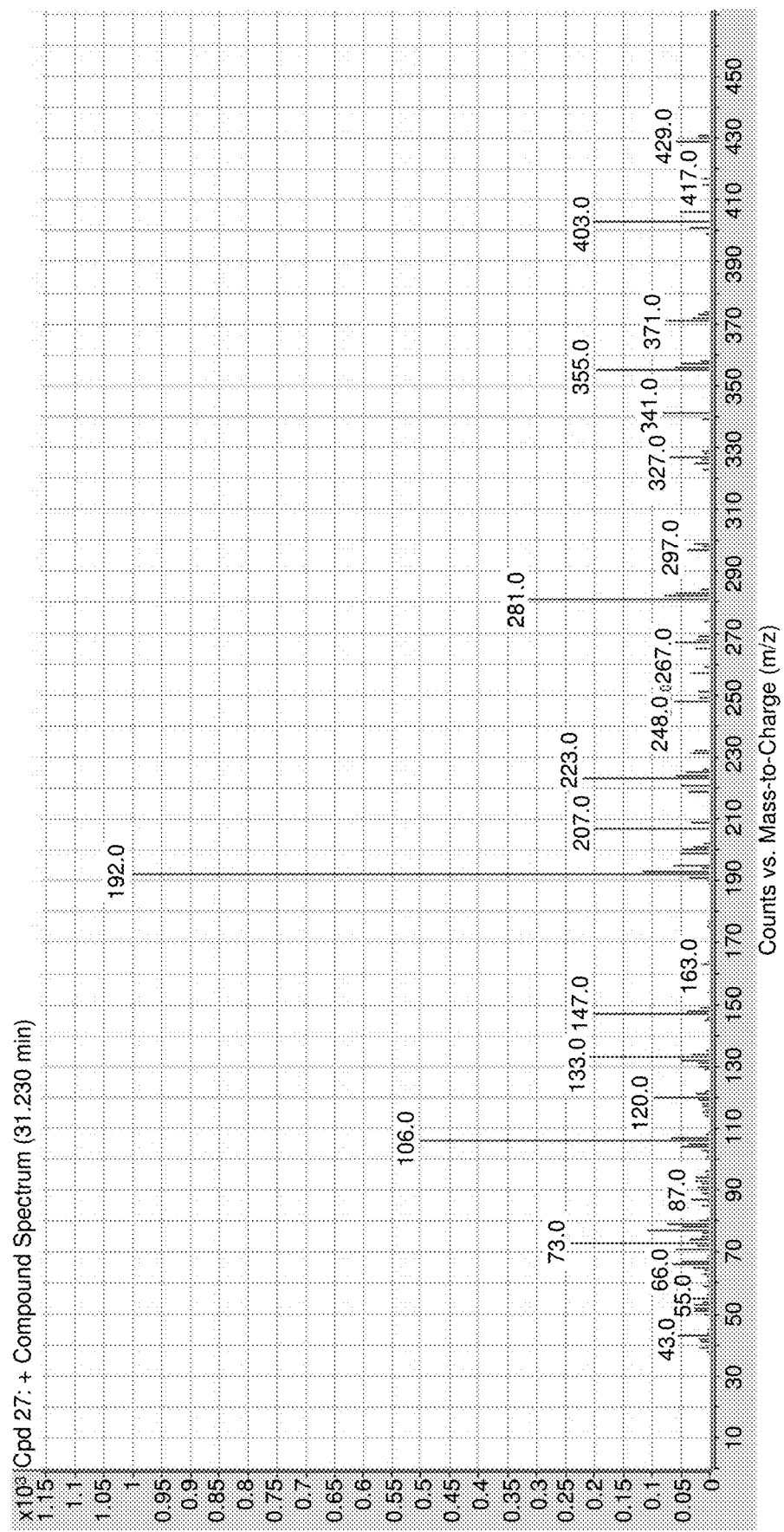

Our experimental setup (summarized in FIG. 4) facilitated headspace volatile monitoring of M. salina with and without the microalgal grazer, B. plicatilis. In each experiment, algal cell concentrations and VOC headspace samples were collected at various time points for M. salina alone (abbreviated Algae or A), M. salina and B. plicatilis (abbreviated Algae+Rotifer or A+R), and ESAW media blanks (abbreviated Media Blank or MB) (FIG. 5 and FIGS. 6A-6N). Significance levels for conditions that exhibited p<0.05 are in Table 1.

At 48 hours after inoculation, algal concentrations across all cultures were similar, approaching the mid- to late-stages of logarithmic growth. At this time, B. plicatilis were added to two M. salina cultures, resulting in time-dependent decreases in algal density relative to controls (FIG. 5). Despite consistent growth conditions, 96 hours after the initial cultures were started and 48 hours after rotifers were added, the Algae+Rotifer cultures displayed different extents of algal biomass loss attributed to rotifer grazing (see, FIG. 5). This variation in rates of biomass loss may arise from differences in rotifer lots.

TABLE 1

List of VOCs in individual experiments 1-3

| | Compound No. | Mass | NIST ID | NIST % Match | Exp. Ret. Index (ERI) | Theor. Ret. Index (TRI) |
|---|---|---|---|---|---|---|
| | | | Experiment 1 | | | |
| A + R cultures | 1 | 208 | | | 1074 | |
| | 2 | 152 | | | 1214 | |
| | 3 | 83 | 2-butanone, 4-(2,6,6-trimethyl-1-cyclohexen-1-yl)- | 70 | 1453 | 1433 |
| | 4 | 177 | trans-β-ionone | 87 | 1506 | 1486 |
| | 5 | 83 | 8-heptadecene | 75 | 1691 | 1719 |
| A + R AND A cultures | 1 | 57 | | | 1134 | |
| | 2 | 148 | | | 1415 | |
| | | | Experiment 2 | | | |
| A + R cultures | 1 | 59 | | | 987 | |
| | 2 | 82 | | | 1021 | |
| | 3 | 71 | octadecanoic acid, ethenyl ester (tentative) | 66 | 1101 | |
| | 4 | 107 | | | 1181 | |
| | 5 | 121 | phenol, 2,3,5-trimethyl- | 71 | 1190 | 1235 |
| | 6 | 137 | 1-cyclohexene-1-carboxaldehyde, 2,6,6-trimethyl- | 89 | 1209 | 1220 |
| | 7 | 121 | 2-butanone, 4-(2,6,6-trimethyl-1-cyclohexen-1-yl)- | 85 | 1443 | 1433 |
| | 8 | 177 | trans-β-ionone | 93 | 1495 | 1486 |
| | 9 | 57 | | | 1692 | |
| | 10 | 143 | | | 1881 | |
| | 11 | 135 | | | 2036 | |
| | 12 | 71 | | | 2115 | |
| A + R AND A cultures | 1 | 55 | hexanoic acid, 2-ethyl-, methyl ester | 68 | 1031 | 1043 |
| | 2 | 96 | 3-nonenoic acid, methyl ester | 73 | 1134 | 1191 |
| | 3 | 341 | | | 1138 | |
| | 4 | 71 | | | 1264 | |
| | 5 | 138 | | | 1338 | |
| | 6 | 73 | | | 1774 | |
| | 7 | 154 | | | 1854 | |
| | 8 | 73 | | | 1983 | |
| | 9 | 73 | | | 2079 | |
| | 10 | 192 | | | 2183 | |
| | 11 | 73 | | | 2210 | |
| A cultures | 1 | 71 | | | 757 | |
| | 2 | 56 | | | 1003 | |
| | 3 | 94 | | | 1207 | |
| | 4 | 91 | | | 1530 | |
| | 5 | 109 | | | 1619 | |
| | 6 | 119 | 2,4-diphenyl-4-methyl-1-pentene | 83 | 1803 | 1846 |
| | 7 | 70 | | | 1955 | |
| | 8 | 70 | | | 2252 | |
| | | | Experiment 3 | | | |
| A + R cultures | 1 | 118 | | | 971 | |
| | 2 | 82 | cyclohexanone, 2,2,6-trimethyl- | 79 | 1021 | 1036 |
| | 3 | 55 | | | 1054 | |
| | 4 | 107 | silane, 1,3-butadiynyltrimethyl-(tentative) | 74 | 1181 | |
| | 5 | 121 | | | 1191 | |
| | 6 | 137 | 1-cyclohexene-1-carboxaldehyde, 2,6,6-trimethyl- | 81 | 1209 | 1220 |
| | 7 | 122 | | | 1379 | |
| | 8 | 121 | 2-butanone, 4-(2,6,6-trimethyl-1-cyclohexen-1-yl)- | 76 | 1419 | 1433 |
| | 9 | 327 | | | 1429 | |
| | 10 | 401 | | | 1458 | |
| | 11 | 177 | trans-β-ionone | 94 | 1495 | 1486 |
| | 12 | 179 | | | 1522 | |
| | 13 | 158 | | | 1675 | |
| | 14 | 57 | | | 1691 | |
| | 15 | 172 | | | 1744 | |
| | 16 | 73 | | | 1744 | |
| | 17 | 150 | | | 1776 | |
| | 18 | 73 | | | 1907 | |
| | 19 | 251 | | | 2406 | |
| | 20 | 73 | | | 2422 | |
| | 21 | 149 | | | 2496 | |
| A + R AND A cultures | 1 | 57 | | | 978 | |
| | 2 | 71 | | | 1039 | |
| | 3 | 96 | 3-nonenoic acid, methyl ester | 74 | 1134 | 1191 |
| | 4 | 341 | | | 1139 | |
| | 5 | 71 | | | 1293 | |
| | 6 | 138 | 2,2,6,7-tetramethyl-10-oxatricyclo[4.3.0.1(1,7)]decan-5-one | 71 | 1338 | |
| | 7 | 71 | | | 1370 | |
| | 8 | 57 | | | 1507 | |

TABLE 1-continued

List of VOCs in individual experiments 1-3

| Compound No. | Mass | NIST ID | NIST % Match | Exp. Ret. Index (ERI) | Theor. Ret. Index (TRI) |
|---|---|---|---|---|---|
| 9 | 73 | | | 1983 | |
| 10 | 192 | | | 2112 | |
| 11 | 192 | | | 2197 | |
| 12 | 73 | | | 2345 | |

Table 2 provides significant difference determination between mean levels of algal cell densities amongst replicates of Algae (*M. salina*), Algae+Rotifer (*M. salina* and *B. plicatilis*) and Media Blank, MB (ESAW) calculated by ANOVA with Tukey's HSD test. Timepoints are reported relative to the addition of algae to the growth media. Rotifers were added to each condition after the 48 hour timepoint.

TABLE 2

Significant difference determination for Experiments 1-3

Experiment 1

| | 24 Hours | 48 Hours | 72 Hours | 96 Hours | 120 Hours |
|---|---|---|---|---|---|
| MB 1 vs MB 2 | — | >0.9999 | 0.9942 | >0.9999 | >0.9999 |
| MB 1 vs A 1 | — | 0.0024 | <0.0001 | <0.0001 | <0.0001 |
| MB 1 vs A 2 | — | 0.0011 | <0.0001 | <0.0001 | <0.0001 |
| MB 1 vs A + R 1 | — | 0.0004 | 0.2087 | 0.2671 | 0.2335 |
| MB 1 vs A + R 2 | — | 0.002 | 0.6522 | 0.9602 | 0.9978 |
| MB 2 vs A 1 | — | 0.0024 | <0.0001 | <0.0001 | <0.0001 |
| MB 2 vs A 2 | — | 0.0011 | <0.0001 | <0.0001 | <0.0001 |
| MB 2 vs A + R 1 | — | 0.0004 | 0.0719 | 0.2662 | 0.2335 |
| MB 2 vs A + R 2 | — | 0.002 | 0.3351 | 0.9598 | 0.9978 |
| A 1 vs A 2 | — | 0.9996 | 0.9827 | >0.9999 | 0.9898 |
| A 1 vs A + R 1 | — | 0.9818 | <0.0001 | <0.0001 | <0.0001 |
| A 1 vs A + R 2 | — | >0.9999 | <0.0001 | <0.0001 | <0.0001 |
| A 2 vs A + R 1 | — | 0.9987 | <0.0001 | <0.0001 | <0.0001 |
| A 2 vs A + R 2 | — | 0.9999 | <0.0001 | <0.0001 | <0.0001 |
| A + R 1 vs A + R 2 | — | 0.9887 | 0.9615 | 0.7415 | 0.455 |

Experiment 2

| | 24 Hours | 48 Hours | 72 Hours | 96 Hours | 120 Hours |
|---|---|---|---|---|---|
| MB 1 vs MB 2 | >0.9999 | >0.9999 | >0.9999 | >0.9999 | >0.9999 |
| MB 1 vs A 1 | 0.0202 | <0.0001 | <0.0001 | <0.0001 | <0.0001 |
| MB 1 vs A 2 | 0.0075 | <0.0001 | <0.0001 | <0.0001 | <0.0001 |
| MB 1 vs A + R 1 | 0.0088 | <0.0001 | <0.0001 | 0.0079 | 0.0051 |
| MB 1 vs A + R 2 | 0.0081 | 0.0001 | <0.0001 | <0.0001 | <0.0001 |
| MB 2 vs A 1 | 0.0202 | <0.0001 | <0.0001 | <0.0001 | <0.0001 |
| MB 2 vs A 2 | 0.0075 | <0.0001 | <0.0001 | <0.0001 | <0.0001 |
| MB 2 vs A + R 1 | 0.0088 | <0.0001 | <0.0001 | 0.008 | 0.0051 |
| MB 2 vs A + R 2 | 0.0081 | 0.0001 | <0.0001 | <0.0001 | <0.0001 |
| A 1 vs A 2 | 0.9987 | >0.9999 | 0.2066 | 0.9996 | 0.6884 |
| A 1 vs A + R 1 | 0.9994 | 0.9999 | 0.9711 | 0.0148 | <0.0001 |
| A 1 vs A + R 2 | 0.9991 | 0.9868 | 0.7331 | 0.8134 | <0.0001 |
| A 2 vs A + R 1 | >0.9999 | 0.9992 | 0.0422 | 0.0069 | <0.0001 |
| A 2 vs A + R 2 | >0.9999 | 0.9723 | 0.9268 | 0.9322 | <0.0001 |
| A + R 1 vs A + R 2 | >0.9999 | 0.9984 | 0.2879 | 0.0006 | 0.0016 |

Experiment 3

| | 24 Hours | 48 Hours | 72 Hours | 96 Hours | 120 Hours |
|---|---|---|---|---|---|
| MB 1 vs MB 2 | >0.9999 | >0.9999 | >0.9999 | >0.9999 | >0.9999 |
| MB 1 vs A 1 | 0.4867 | 0.0696 | <0.0001 | <0.0001 | <0.0001 |
| MB 1 vs A 2 | 0.3291 | 0.0136 | <0.0001 | <0.0001 | <0.0001 |
| MB 1 vs A + R 1 | 0.2848 | 0.0115 | 0.0001 | <0.0001 | <0.0001 |
| MB 1 vs A + R 2 | 0.2356 | 0.0086 | 0.0002 | <0.0001 | <0.0001 |
| MB 2 vs A 1 | 0.4861 | 0.069 | <0.0001 | <0.0001 | <0.0001 |
| MB 2 vs A 2 | 0.3286 | 0.0135 | <0.0001 | <0.0001 | <0.0001 |
| MB 2 vs A + R 1 | 0.2844 | 0.0114 | 0.0001 | <0.0001 | <0.0001 |
| MB 2 vs A + R 2 | 0.2352 | 0.0085 | 0.0002 | <0.0001 | <0.0001 |
| A 1 vs A 2 | 0.9997 | 0.9814 | 0.8709 | 0.6052 | 0.9915 |
| A 1 vs A + R 1 | 0.999 | 0.9722 | 0.9966 | 0.7581 | 0.1778 |
| A 1 vs A + R 2 | 0.9964 | 0.9503 | 0.9866 | 0.0302 | 0.064 |
| A 2 vs A + R 1 | >0.9999 | >0.9999 | 0.6082 | 0.0622 | 0.0533 |
| A 2 vs A + R 2 | >0.9999 | >0.9999 | 0.5053 | 0.0005 | 0.0163 |
| A + R 1 vs A + R 2 | >0.9999 | >0.9999 | >0.9999 | 0.4138 | 0.9958 |

"—" indicates no measurements were taken.

Example 4: Headspace VOC Results

Headspace VOCs were sampled with SPME fibers for 30-60 min each at various time points (as indicated in FIG. 5) and analyzed by GC-MS. Qualitative and quantitative differences were observed in the VOC profiles of Algae+Rotifer cultures compared to the Algae cultures. Example total ion chromatograms for Algae and Algae+Rotifer cultures taken approximately 24 hours after addition of rotifers (Experiment #3) are shown in FIG. 7A. Several VOCs that differentiate the two culture conditions are enumerated (FIG. 7A, annotations in Table 3) and are potential early indicators of algal grazing or death.

TABLE 3

VOCs robustly and repeatedly detected from Algae (A) and Algae + Rotifer (A + R) experiments

| | | | | | | Ret. Index (RI) | | Exp. No. | | |
|---|---|---|---|---|---|---|---|---|---|---|
| Tentative compound | No. | Mass | class* | NIST14 ID | NIST % match | Exp. | Theor. | 1 | 2 | 3 |
| VOCs detected in A + R cultures | 1 | 82 | carotenoid | 2,2,6-trimethylcyclo-hexanone | 79 | 1021 | 1036 | | X | X |
| | 2 | 107 | | | | 1181 | | X | X | X |
| | 3 | 121 | phenol | | | 1191 | | | X | X |
| | 4 | 137 | carotenoid | 2,6,6-trimethyl-1-cyclohexene-1-carboxaldehyde | 81 | 1209 | 1220 | X | X | X |

TABLE 3-continued

VOCs robustly and repeatedly detected from Algae (A) and Algae + Rotifer (A + R) experiments

| | | Tentative compound | | NIST % | Ret. Index (RI) | | Exp. No. | | |
|---|---|---|---|---|---|---|---|---|---|
| | No. | Mass | class* | NIST14 ID | match | Exp. | Theor. | 1 | 2 | 3 |
| | 5 | 121 | carotenoid | 4-(2,6,6-trimethyl-1-cyclohexen-1-yl)-2-butanone | 76 | 1419 | 1433 | X | X | X |
| | 6 | 177 | carotenoid | trans-β-ionone | 94 | 1495 | 1486 | X | X | X |
| | 7 | 57 | alkane | | | 1691 | | X | X | X |
| VOCs detected in | 8 | 71 | | | | 1039 | | | X | X |
| A + R and A | 9 | 96 | methyl ester | 3-nonenoic acid, methyl ester | 74 | 1134 | 1191 | X | X | X |
| cultures | 10 | 34 | | | | 1139 | | | X | X |
| | 11 | 71 | | | | 1293 | | | X | X |
| | 12 | 138 | terpene/carotenoid | | | 1338 | | | X | X |
| | 13 | 73 | fatty acid (hexadecenoic acid) | | | 1983 | | | X | X |
| | 14 | 192 | | | | 2197 | | | X | X |

*Tentative compound class for unknown compounds is based on fragmentation in averaged mass spectra determined via chromatographic deconvolution and alignment.

Extracted ion chromatograms were utilized to improve visualization of individual VOCs. FIGS. 7B-7D demonstrate the increase in an VOC displaying a base peak m/z 177 and retention index (RI) 1495, observed over the time course of the experiment in Algae+Rotifer cultures. Although the Algae chromatogram for m/z 177 also displays a small peak at the same retention time, this VOC was not detected using the given experimental criteria for data processing.

The number of compounds detected from deconvolution of chromatographic peaks varied with each sample. The analysis of a single sample commonly detected 100-200 chemical compounds, many of which were attributed to background (known from control measurements). Application of chromatographic peak alignment across the data from all samples and at every timepoint generated a list of more than 1800 compounds, consisting of both algal VOCs and extraneous signals from the experimental setup. Many compounds were attributed to known background or were not found reproducibly. Application of the filtering criteria based upon algal abundance and detection frequency across experimental replicates identified the most robust compounds as potential VOC biomarkers from either Algae or Algae+Rotifer cultures, removed irreproducible compounds, and narrowed the extensive list to ~50 compounds in any single experiment. Table 3 shows biomarkers that were only observed across multiple experiments. For a detailed list of the volatile biomarkers detected in each experiment, refer to Table 1.

Comparison of three replicate experimental infections of both Algae and Algae+Rotifer cultures revealed several VOCs that were reproducibly observed in 1) Algae+Rotifer cultures and 2) both Algae and Algae+Rotifer cultures, represented in Table 3, despite the different rates in algal biomass loss. For example, Compound 6 monitored in FIGS. 7B-7D was identified with a 94% confidence score as trans-β-ionone using the NIST14 library. Confidence in this identification increases when considering the calculated experimental retention index (RI) of 1495 was within 5% of the literature theoretical value (1486, NIST 14 database).

Within the Algae+Rotifer cultures, all of the discriminating VOCs were structurally-related ketones or aldehydes: (a) Compound 6: trans-β-ionone [IUPAC name: (E)-4-(2,6,6-trimethyl-1-cyclohexen-1-yl)-3-buten-2-one], (b) Compound 4: β-cyclocitral [IUPAC name: 2,6,6-trimethyl-1-cyclohexene-1-carboxaldehyde], (c) Compound 1: 2,2,6-trimethyl-cyclohexanone, and (d) Compound 5: 4-(2,6,6-trimethyl-1-cyclohexene-1-yl)-2-butanone. We propose these compounds as potential biomarkers indicative of algal stress or death. The VOCs observed in both Algae and Algae+Rotifer cultures were most likely algae-derived volatiles universally present in both conditions, with 3-nonenoic acid methyl ester having an adequate confidence for identification (74% spectral match, <5% RI deviation from theoretical value).

For those VOCs that could not be identified using the initial conservative thresholds, the observed spectra and experimental retention indices provided suggestions for their identification. The suggested compound classes for unknown compounds are provided in Table 3, and their experimental mass spectra are included in FIGS. 6A-6N. For example, the mass spectrum of Compound 12 has similar features to those of the identified carotenoids, suggesting a terpenoid structure with a molecular weight of 208 Da. The mass spectrum of Compound 13 contains characteristic ions of hexadecenoic acid including m/z 43, 60, 73, 129, 213, and 256 (M+), and its experimental RI is within 1% of the literature RI of hexadecanoic acid.

Example 5: Abundance of VOCs

In addition to the qualitative analysis, we examined the relationship between rotifer duration of feeding and the abundance of Algae+Rotifer distinguishing VOCs. Levels of Compounds 4 and 6 were compared for individual rotifer cultures (Carboys 5 and 6) across individual experiments (FIG. 8). While there was no detected signal from either compound before the addition of rotifers (48 hours), all detected signals after rotifer addition exceeded $2.0 \times 10^5$ counts, 2-3 orders of magnitude above detection threshold.

Another carotenoid oxidation product, β-cyclocitral, appeared in Experiment 2 after 24 hours of rotifer feeding, with the signal increasing to more than $6.0 \times 10^5$ counts after 48 hours of rotifer feeding. Similar comparisons for Compounds 1-7 are included in FIGS. 9A-9C. Of note, comparison of FIG. 8 to FIG. 5 reveals several instances where these VOCs were detected in Algae+Rotifer cultures before biomass loss was apparent as compared to algae controls. For example, the second biological replicate of Algae+Rotifers in experiment 2 did not differ in algal density from the healthy controls at the 72 h and 96 h timepoints. However, the signals for Compounds 4 and 6 were already large ($6.0 \times 10^5$ and $1.0 \times 10^6$ counts, respectively).

Example 6: Discussion of Chemical Profiling Data

Our SPME-GC-MS analysis has identified seven discriminating VOCs in *M. salina* cultures in the presence of actively-grazing *B. plicatilis* (Algae+Rotifer). The absence of these volatiles in the time-matched Algae control cultures suggests these chemicals are specific signals of algal grazing or algal death. Many of these chemicals were detected within 24 hours after rotifer addition and before algal cell densities changed substantially.

Specifically, Compounds 4, 5, 6, and 7 were identified as early and robust grazing signals observed in *M. salina* cultures containing rotifers. Several identified biomarkers—Compounds 1, 4, 5, 6 and 7—were detected only during rotifer grazing and contained structural similarities, hinting at a shared metabolic pathway. Many of these compounds (Table 3) are known products of carotenoid oxidation.[31, 32] Carotenoid-derived substances have been previously observed in microalgal volatile research, largely associated with investigations of flavor or smell components in food production. Carotenoids have important physiological functions as a component of photosystems—the light-harvesting complexes that transfer light energy to chlorophyll.[33] Oxidative cleavage of the carotenoid backbone can occur through enzymatic (carotenoid cleavage dioxygenases) or non-enzymatic (light, oxygen, temperature) mechanisms.[33] Potential pathways for oxidative cleavage of the carotenoid β-carotene are shown in FIG. 10.

In our work, the carotenoid-derived VOCs could be generated from the oxidation of β-carotene released upon lysis of *M. salina* cells during the digestive process of *B. plicatilis*. This would be in agreement with studies of *Arabidopsis* plants exposed to reactive oxygen species resulting in the subsequent release of β-ionone and β-cyclocitral.[34] The results from vascular plants suggest that carotenoid degradation products may be more general indicators of stressed or wounded algae cultures, not solely limited to the interaction of algae with rotifers.

Although there are no reports of such analyses of *M. salina*, a small number of studies have examined algae from the genus *Nannochloropsis*, of which *M. salina* is a close relative[35]. For instance, Van Durme et al.[36] investigated the volatile composition of five microalgae species (*Botryococcus braunii, Rhodomonas, Tetraselmis* sp., *Nannochloropsis oculata*, and *Chlorella vulgaris*) by heating samples (40° C.) to produce volatile signatures under heat stress conditions. Products of carotenoid oxidation, including α- or β-ionone and β-cyclocitral, were identified in all species tested.

Interestingly, *N. oculata* contained a large abundance of ethanol, 2-hydroxy-2-butanone, and benzaldehyde, while only small amounts of β-cyclocitral and ionones were detected. Hosoglu[37] likewise characterized the volatilomes of several microalgae species using SPME-GC-MS and GC-olfactometry for both chemical profiles and olfactory properties to benefit incorporation into food products and to minimize unpleasant smells. The species *C. vulgaris, C. protothecoides*, and *T. chuii* reportedly contain distinguishing amounts of the carotenoid degradation products, α- and β-ionone and 6-methyl-5-hepten-2-one, while expressing a woody smell.

While VOCs have been observed in analyses of chemical compositions of algae in destructive manners (i.e., heating, sonication, solvent extraction, etc.), there are fewer reports of volatiles emitted from live, actively-growing cultures. A variety of live algae-derived volatiles (terpenoids, aldehydes, halogenated compounds, etc.) have been shown to influence the odor quality of water.[26] Zhou et al.[38] investigated changes in the volatilome of intact algae over different growth phases (logarithmic, stationary, and decline phase) for six microalgae (*Thalassiosira weissflogii, Nitzschia closterium, Chaetoceros calcitrans, Platymonas helgolandica, Nannochloropsis* spp. (NMBluh014-1), and *Dicrateria inornate*). The *Nannochloropsis* volatilome was largely dominated by alkanes and alkenes and 8-heptadecene, but no carotenoid by-products were reported. Several functions for actively-released VOCs, including carotenoids, have been postulated, such as tolerance of light and oxidative stressors, signaling the presence of predators,[33] and transfer of information throughout algal colonies.[26] β-cyclocitral has previously been reported as a volatile emitted by the bloom-forming cyanobacterium Microcystis as a defense mechanism against grazing by *Daphnia magna*.[39]

Our work focused on the volatiles generated from active grazing of algae, which will generate more rapid algal death compared to natural growth cycles. Here, we confirmed the importance of β-cyclocitral as an indication of algal cell damage due to grazing. Future work will determine if VOCs produced by *M. salina* in the presence of *B. plicatilis* has a similar role in algal-defense as observed previously.

Using a non-invasive, non-destructive sampling and analysis technique, we have demonstrated that VOCs from the headspace of algae cultures can distinguish between algae cultures with grazing rotifers present and uninfected algal cultures, and may serve as general indicators of algal cell death. In order to discover and validate additional diagnostic markers of grazer infection or other incipient crashes, more extensive study of emitted volatiles from microalgal species is required. For example, low levels of grazer-associated VOCs in healthy algal cultures may result from background rates of algal death. Such background signals are likely modulated by physiological state of the culture (e.g. exponential growth or stationary phase) or by nutrient limitation. Thus, an improved understanding of the threshold biomarker concentrations that indicate the need for interdictive treatment is paramount.

It is also worth noting that the list of biomarkers reported in this analysis may be considered conservative owing to the stringency of our filtering criteria. Additional biomarkers may be observed with less stringent parameters for the filtration of detected VOC peaks in data processing. However, the identified carotenoid breakdown products served as indicators for algal crashes across all three experiments.

Additionally, our SPME-GC-MS methodology is expected to have broader applications. Complex systems-level dynamics between algae, commensal bacteria, and various grazers will require more sophisticated sampling procedures alongside volatilomics data to include biological data sets, such as transcriptomics, metagenomics, and metabolomics. These systems-level analyses and bioinformatics analysis would be more likely to elucidate biological interactions or implications for the chemicals observed in the volatilome. Non-invasive and non-destructive VOC sampling is an attractive, analytical way to better understand and predict the health of microbial cultures.

In conclusion, our work aims to increase the breadth and depth of reported algal and rotifer-specific VOCs, providing a tool to better define the physiological state of microalgal ponds and facilitate greater algal biomass production. A SPME-GC-MS methodology for non-invasive and non-destructive sampling of *M. salina* infected by *B. plicatilis* aided our discovery of seven putative culture crash biomarkers, including trans-β-ionone and β-cyclocitral, over several timepoints during active crashing of algal ponds. These biomarkers were not detected in cultures displaying natural background levels of cell death, suggesting that these signals are produced by high stress conditions, such as rotifer grazing. Finally, these biomarkers offer potential as diagnostic tools to signal the need for crash mitigation strategies, as several signals were detectable before cell death was evident from changes in cell density.

Both VOC baselines and signatures from multiple healthy and infected cultures could be compiled in a data base. Early use of this technique would then include surveilling for the emergence of targeted VOC biomarkers of algal distress or injury above healthy baseline thresholds that are indicative of imminent culture failure.

We envision the use of VOC based monitoring in open ponds and we are in the process of extending this work to such systems. In such environments, one must take into account that the volatile "headspace" of open ponds may be influenced by external sources (e.g. VOCs from the environment, wind effects, particulates, etc.), creating a variable background that would require correction for the levels of biomarker compounds. It is possible to temporarily create closed "headspace" above an area of open pond (perhaps using a large funnel), during sample collection, which would serve to limit outside "noise".

The SPME fibers used in this experiment are field deployable and can easily be adapted to an algal pond production system. Although SPME-GC-MS has proven powerful for untargeted discovery of algal volatile chemical signatures from healthy or grazed cultures, the cost of state-of-the art laboratory-based GC-MS systems and analyses efforts is prohibitive for using this method for continuous monitoring of industrial scale, open algal ponds.

Knowledge gained and biomarkers annotated from our untargeted discovery efforts may guide development of targeted, lower-cost, field-deployable detectors capable of monitoring for changes in diagnostic chemical signatures and detecting volatile signals of infection in real-time to facilitate the timely deployment interdictive strategies to prevent pond crashes. Miniaturized GC-MS systems[40, 41] for field deployable detector systems is one such technology currently under development and optimization[42] for this type of application.

REFERENCES

1. Hannon M et al., "Biofuels from algae: challenges and potential," *Biofuels* 2010; 1:763-84.
2. Leite G B et al., "Algal biofuels: challenges and opportunities," *Bioresour. Technol.* 2013; 145:134-41.
3. Katiyar R et al., "Microalgae based biofuel: challenges and opportunities," in *Biofuels: Technology, Challenges and Prospects* (Agarwal A K, Agarwal R A, Gupta T, & Gurjar B R, eds.), Springer Singapore (Singapore, 2017), pp. 157-75.
4. Richardson J W et al., "A financial assessment of two alternative cultivation systems and their contributions to algae biofuel economic viability," *Algal Res.* 2014; 4:96-104.
5. Day J G et al., "Microzooplanktonic grazers—a potentially devastating threat to the commercial success of microalgal mass culture," *Algal. Res.* 2017; 27:356-65.
6. Carney L T & Lane T W, "Parasites in algae mass culture," *Front. Microbiol.* 2014; 5: 278 (8 pp.).
7. Hirayama K & Ogawa S, "Fundamental studies on physiology of rotifer for its mass culture-I: filter feeding of rotifer," *Nippon Suisan Gakkaishi* [*Bull. Japan. Soc. Sci. Fisheries*] 1972; 38:1207-14.
8. McBride R C et al., "Contamination management in low cost open algae ponds for biofuels production," *Indust. Biotechnol.* 2014; 10:221-7.
9. Park S et al., "The selective use of hypochlorite to prevent pond crashes for algae-biofuel production," *Water Environ. Res.* 2016; 88:70-8.
10. Pradeep V et al., "Use of copper to selectively inhibit *Brachionus calyciflorus* (predator) growth in *Chlorella kessleri* (prey) mass cultures for algae biodiesel production," Int. *J. Mol. Sci.* 2015; 16:20674-84.
11. Fott B, "*Phlyctidium scenedesmi* spec. nova, a new chytrid destroying mass cultures of algae," *Zeitschrift für allgemeine Mikrobiologie* [*J. Basic Microbiol.*] 1967; 7:97-102.
12. Xu C et al., "The use of the schizonticidal agent quinine sulfate to prevent pond crashes for algal-biofuel production," *Int. J. Mol. Sci.* 2015; 16:27450-6.
13. Van Ginkel S W et al., "Taking advantage of rotifer sensitivity to rotenone to prevent pond crashes for algal-biofuel production," *Algal Res.* 2015; 10:100-3.
14. Liu Z & Lu G, "The sterilizing studies of flagellate and cilitate in marine unicellular algae liquid," *Zhanjiang Aquacult. Coll.* 1990; 6:36-41.
15. Wang H et al., "The contamination and control of biological pollutants in mass cultivation of microalgae," *Bioresour. Technol.* 2013; 128:745-50.
16. Fisher C L et al., "Bacterial communities protect the alga *Microchloropsis salina* from grazing by the rotifer *Brachionus plicatilis,*" *Algal Res.* 2019; 40:101500 (9 pp.).
17. United States Department of Energy, "Bioenergy Technologies Office: Multi-Year Program Plan," *DOE Report No. DOE/EE*-0915, Washington, DC, May 2013 (190 pp.).
18. Borowitzka M A, "Chapter 14: Culturing microalgae in outdoor ponds," in *Algal Culturing Techniques* (Andersen R A, ed.), Elsevier Academic Press (Oxford, U K, 2005), pp. 205-18.
19. Day J G et al., "Early detection of protozoan grazers in algal biofuel cultures," *Bioresour. Technol.* 2012; 114: 715-9.
20. Wang Y et al., "Early detection and quantification of zooplankton grazers in algal cultures by FlowCAM," *Algal Res.* 2017; 21:98-102.
21. Carney L T et al., "Chapter 8: Molecular Diagnostic Solutions in Algal Cultivation Systems," in *Microalgal Production for Biomass and High-Value Products* (Slocombe S P & Benemann J R, eds.), CRC Press (Boca Raton, L A, 2016), pp. 183-204.
22. Carney L T et al., "Pond Crash Forensics: Presumptive identification of pond crash agents by next generation sequencing in replicate raceway mass cultures of *Nannochloropsis salina,*" *Algal Res.* 2016; 17:341-7.
23. Achyuthan K E et al., "Volatile metabolites emission by in vivo microalgae—an overlooked opportunity?," *Metabolites* 2017; 7:39 (46 pp.).
24. Rowan D D, "Volatile metabolites," *Metabolites* 2011; 1:41-63.
25. Leach J E et al., "Communication in the phytobiome," *Cell* 2017; 169:587-96.
26. Zuo Z, "Why algae release volatile organic compounds—the emission and roles," *Front. Microbiol.* 2019; 10:491 (7 pp.).
27. Wolfe G V & Steinke M, "Grazing-activated production of dimethyl sulfide (DMS) by two clones of Emiliania huxleyi," *Limnol. Oceanogr.* 1996; 41:1151-60.

28. Wolfe G V et al., "Release and consumption of DMSP from Emiliania huxleyi during grazing by *Oxyrrhis marina*," *Mar. Ecol. Prog. Ser.* 1994; 111:111-9.
29. Wolfe G V et al., "Grazing-activated chemical defence in a unicellular marine alga," *Nature* 1997; 387:894-7.
30. Hay M E, "Marine chemical ecology: chemical signals and cues structure marine populations, communities, and ecosystems," *Ann. Rev. Mar. Sci.* 2009; 1:193-212.
31. de Jesus Benevides C M et al., "A chemical study of β-carotene oxidation by ozone in an organic model system and the identification of the resulting products," *Food Chem.* 2011; 126:927-34.
32. Christaki E et al., "Functional properties of carotenoids originating from algae," *J. Sci. Food Agric.* 2013; 93:5-11.
33. Havaux M, "Carotenoid oxidation products as stress signals in plants," *Plant J.* 2014; 79:597-606.
34. Ramel F et al., "Carotenoid oxidation products are stress signals that mediate gene responses to singlet oxygen in plants," *Proc. Nat'l Acad. Sci. USA* 2012; 109:5535-40.
35. Fawley M W et al., "The phylogeny of the genus *Nannochloropsis* (Monodopsidaceae, Eustigmatophyceae), with descriptions of *N. australis* sp. nov. and *Microchloropsis* gen. nov.," *Phycologia* 2015; 54:545-52.
36. Van Durme J et al., "Evaluation of the volatile composition and sensory properties of five species of microalgae," *J. Agric. Food Chem.* 2013; 61:10881-90.
37. Isleten Hosoglu M, "Aroma characterization of five microalgae species using solid-phase microextraction and gas chromatography-mass spectrometry/olfactometry," *Food Chem.* 2018; 240:1210-8.
38. Zhou L et al., "Change of volatile components in six microalgae with different growth phases," *J. Sci. Food Agric.* 2017; 97:761-9.
39. Jüttner F et al., "β-cyclocitral, a grazer defence signal unique to the cyanobacterium Microcystis," *J. Chem. Ecol.* 2010; 36:1387-97.
40. Whiting J J et al., "A high-speed, high-performance, microfabricated comprehensive two-dimensional gas chromatograph," *Lab Chip* 2019; 19:1633-43.
41. Lewis P R et al., "Recent advancements in the gas-phase MicroChemLab," *IEEE Sensors J.* 2006; 6:784-95.
42. Snyder, D T et al., "Miniature and fieldable mass spectrometers: recent advances," *Anal. Chem.* 2016; 88:2-29.
43. Fisher C & Lane T W, "Operational, prophylactic, and interdictive technologies in algal crop protection," in *Grand Challenges in Algae Biotechnology* (Hallmann A & Rampelotto P H, eds.), Springer International Publishing (Cham, Switzerland, 2019).
44. Reese K L et al., "Chemical profiling of volatile organic compounds in the headspace of algal cultures as early biomarkers of algal pond crashes," *Sci. Rep.* 2019; 9:13866 (10 pp.) and Supplemental Data File (15 pp.).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of detecting crop damage in an algal culture, the method comprising:
    detecting one or more carotenoids as a volatile organic compound within a first sample obtained from a headspace of the algal culture, thereby indicating presence of crop damage.

2. The method of claim 1, wherein the detecting step comprises employing one or more solid-phase microextraction fibers coupled with gas chromatography-mass spectrometry.

3. The method of claim 1, wherein the carotenoid has a structure of formula (I):

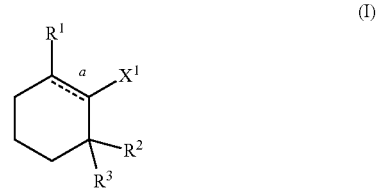

or a salt thereof, wherein:
    each of $R^1$, $R^2$, and $R^3$ is, independently, H, optionally substituted alkyl, or optionally substituted alkenyl;
    $X^1$ is oxo, optionally substituted alkyl, optionally substituted alkenyl, or optionally substituted acyl; and
    the dashed double bond indicated at position a may be present or absent.

4. The method of claim 1, wherein the carotenoid has a structure of formula (II):

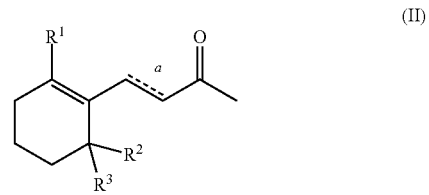

or a salt thereof, wherein:
    each of $R^1$, $R^2$, and $R^3$ is, independently, H, optionally substituted alkyl, or optionally substituted alkenyl; and
    the dashed double bond indicated at position a may be present or absent.

5. The method of claim 1, wherein the carotenoid is trans-β-ionone and/or β-cyclocitral.

6. The method of claim 1, wherein the carotenoid is selected from the group consisting of trans-β-ionone, β-cyclocitral, 2,2,6-trimethylcyclohexanone, and 4-(2,6,6-trimethyl-1-cyclohexen-1-yl)-2-butanone.

7. The method of claim 1, wherein the crop damage is from a rotifer.

8. The method of claim 1, further comprising:
detecting one or more further carotenoids as a volatile organic compound within a second sample obtained from the headspace of the algal culture, wherein the second sample is obtained of from about 10 minutes to about 72 hours after the first sample.

9. The method of claim 8, wherein the carotenoid from the first sample and the further carotenoid from the second sample are the same.

10. The method of claim 9, wherein a detected amount of the further carotenoid from the second sample is greater than a detected amount of the carotenoid from the first sample.

11. A method of detecting crop damage in an algal culture, the method comprising:
detecting one or more carotenoids as a volatile organic compound within a first sample obtained from a headspace of the algal culture; and
further detecting the one or more carotenoids as a volatile organic compound within a second sample obtained from the headspace of the algal culture, wherein the second sample is obtained after the first sample, thereby indicating presence of crop damage.

12. The method of claim 11, wherein the carotenoid has a structure of formula (I):

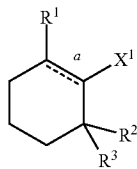

(I)

or a salt thereof, wherein:
each of $R^1$, $R^2$, and $R^3$ is, independently, H or optionally substituted alkyl;
$X^1$ is oxo, optionally substituted alkyl, optionally substituted alkenyl, or optionally substituted acyl; and
the double bond indicated at position a may be present or absent.

13. The method of claim 11, wherein the carotenoid has a structure of formula (II):

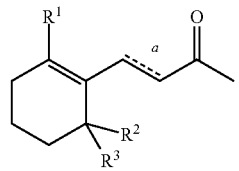

(II)

or a salt thereof, wherein:
each of $R^1$, $R^2$, and $R^3$ is, independently, H or optionally substituted alkyl; and
the double bond indicated at position a may be present or absent.

14. The method of claim 11, wherein the carotenoid is trans-β-ionone and/or β-cyclocitral.

15. The method of claim 11, wherein the carotenoid is selected from the group consisting of trans-β-ionone, β-cyclocitral, 2,2,6-trimethylcyclohexanone, and 4-(2,6,6-trimethyl-1-cyclohexen-1-yl)-2-butanone.

16. The method of claim 11, wherein the crop damage is from a rotifer.

17. The method of claim 11, wherein the second sample is obtained of from about 10 minutes to about 72 hours after the first sample.

18. The method of claim 11, wherein a detected amount of the carotenoid from the second sample is greater than a detected amount of the carotenoid from the first sample.

19. The method of claim 11, wherein a detected amount of trans-β-ionone and/or β-cyclocitral from the second sample is greater than a detected amount of a trans-β-ionone and/or β-cyclocitral from the first sample.

20. The method of claim 11, further comprising, after the further detecting step:
providing one or more additives to protect the algal culture from damage;
the one or more additives selected from the group consisting of: Alphaproteobacteria, Rhodobacteraceae, *Roseobacter, Ruegeria, Paracoccus, Phenylobacterium*, Actinobacteria, *Dietzia*, Cytophagia, *Marinoscillum*), Gammaproteobacteria, *Marinobacter, Pseudomonas, Alteromonas, Methylophaga*, pesticide, biocide, rotenone, tossendanin, quinine, quinine sulfate, formaldehyde, ammonia, an oxidant, hydrogen peroxide, hypochlorite, copper, or salts of any of these.

* * * * *